(12) United States Patent
Yoshida

(10) Patent No.: US 10,096,916 B2
(45) Date of Patent: Oct. 9, 2018

(54) TERMINAL MEMBER AND CONNECTOR

(71) Applicant: NGK Spark Plug Co., LTD., Nagoya (JP)

(72) Inventor: Shingo Yoshida, Ichinomiya (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 0 days.

(21) Appl. No.: 15/604,100

(22) Filed: May 24, 2017

(65) Prior Publication Data

US 2017/0346201 A1 Nov. 30, 2017

(30) Foreign Application Priority Data

May 30, 2016 (JP) .................................. 2016-107631
May 15, 2017 (JP) .................................. 2017-096645

(51) Int. Cl.
| | |
|---|---|
| *H01R 12/58* | (2011.01) |
| *H01R 12/51* | (2011.01) |
| *H01R 43/20* | (2006.01) |
| *H01R 4/18* | (2006.01) |
| *G01N 33/00* | (2006.01) |
| *G01N 27/41* | (2006.01) |
| *G01N 27/409* | (2006.01) |
| *G01M 15/10* | (2006.01) |

(52) U.S. Cl.
CPC ......... *H01R 12/585* (2013.01); *G01N 27/409* (2013.01); *G01N 27/41* (2013.01); *G01N 33/0036* (2013.01); *H01R 4/184* (2013.01); *H01R 12/515* (2013.01); *H01R 43/205* (2013.01); *G01M 15/102* (2013.01)

(58) Field of Classification Search
CPC ........ H01R 4/183; H01R 4/184; H01R 4/185; H01R 13/405; H01R 43/24
USPC .............................. 439/733.1, 736, 751, 744
See application file for complete search history.

(56) References Cited

U.S. PATENT DOCUMENTS

| | | | | |
|---|---|---|---|---|
| 4,029,388 A | * | 6/1977 | Knoll .................... | H01R 13/405 249/96 |
| 4,579,404 A | * | 4/1986 | Lockard ................. | H01R 12/75 439/497 |
| 5,139,446 A | * | 8/1992 | Costello ................. | H01R 13/42 439/751 |
| 5,338,231 A | * | 8/1994 | Wilhite .............. | H01R 13/2442 439/660 |
| 5,409,404 A | * | 4/1995 | Reed .................... | H01R 13/405 439/396 |

(Continued)

FOREIGN PATENT DOCUMENTS

JP 5307878 B 10/2013

*Primary Examiner* — Ross Gushi
(74) *Attorney, Agent, or Firm* — Leason Ellis LLP

(57) ABSTRACT

A connector has a fixing hole in an intermediate portion of a terminal member, and has an engagement portion projecting downward in a thickness direction, at an end portion at a front end side of the fixing hole. Therefore, when the terminal member is attached to a housing, movement of the terminal member toward a rear end side can be restricted by fitting a projection portion of the housing into the fixing hole. Furthermore, since the engagement portion is provided to the terminal member, movement of the terminal member toward the rear end side can be restricted by engaging the engagement portion with a front end surface of a protrusion portion of the housing.

17 Claims, 19 Drawing Sheets

(56) References Cited

U.S. PATENT DOCUMENTS

| | | | | |
|---|---|---|---|---|
| 5,433,628 A * | 7/1995 | Sadaishi | H01R 4/64 | 29/883 |
| 5,711,067 A * | 1/1998 | Jenner | H01R 4/2429 | 29/874 |
| 6,007,387 A * | 12/1999 | Uchiyama | B29C 45/14639 | 439/736 |
| 6,050,842 A * | 4/2000 | Ferrill | H01R 4/2429 | 439/404 |
| 6,206,735 B1 * | 3/2001 | Zanolli | H01R 12/585 | 439/404 |
| 6,219,913 B1 * | 4/2001 | Uchiyama | B29C 45/14639 | 264/272.11 |
| 6,247,974 B1 * | 6/2001 | Jenner | H01R 4/2429 | 439/403 |
| 6,592,382 B2 * | 7/2003 | Wurster | H05K 3/366 | 439/82 |
| 6,799,988 B2 * | 10/2004 | Mansur | H01R 4/2429 | 439/404 |
| 6,802,736 B2 * | 10/2004 | Godefroy | H01R 13/4223 | 439/492 |
| 6,988,916 B2 * | 1/2006 | Taguchi | H01R 13/405 | 439/862 |
| 7,037,145 B2 * | 5/2006 | Fleming | H01R 9/16 | 439/741 |
| 7,125,286 B2 * | 10/2006 | Wang | H01R 12/58 | 439/637 |
| 7,632,153 B1 * | 12/2009 | Lai | H01R 13/405 | 29/883 |
| 7,901,247 B2 * | 3/2011 | Ring | H01R 13/405 | 439/606 |
| 8,282,426 B2 * | 10/2012 | Zweigle | H01R 13/41 | 439/499 |
| 8,771,025 B2 * | 7/2014 | Lee | H01R 43/24 | 439/693 |
| 9,337,569 B2 * | 5/2016 | Kindermann | H01R 13/41 | |
| 9,466,910 B2 * | 10/2016 | Lee | H01R 13/405 | |
| 9,564,705 B2 * | 2/2017 | Arai | H01R 13/405 | |
| 9,608,359 B2 * | 3/2017 | Arai | H01R 12/716 | |
| 2002/0048999 A1 * | 4/2002 | Ming-Hui | H01R 13/2442 | 439/660 |
| 2009/0098779 A1 * | 4/2009 | Kawamura | H01R 9/032 | 439/733.1 |
| 2012/0164850 A1 | 6/2012 | Kobayashi et al. | | |
| 2016/0036155 A1 * | 2/2016 | Kataoka | H01R 13/405 | 439/736 |

* cited by examiner

TERMINAL MEMBER AND CONNECTOR

This application claims the benefit of Japanese Patent Applications No. 2016-107631, filed May 30, 2016 and No. 2017-096645, filed May 15, 2017, all of which are incorporated herein by reference in their entireties.

FIELD OF THE INVENTION

The present invention relates to a terminal member to be connected to, for example, a sensor or the like, and a connector including the terminal member.

BACKGROUND OF THE INVENTION

Conventionally, as a configuration for connecting a circuit board and a signal wire (lead wire) from, for example, a sensor, a connector in which a terminal member to which the lead wire is connected is fixed to a housing has been used. For example, a sensor device has been known in which a terminal member extending from a connector and a circuit side terminal extending from a circuit board are connected to each other through male-female fitting (see, for example, Japanese Patent No. 5307878).

Problems to be Solved by the Invention

However, in the above-described conventional art, the terminal member and the circuit side terminal are connected to each other through male-female fitting in an axial direction of the terminal member, and thus the following problem may occur.

Specifically, an electrical connection is established by contact between a male terminal and a female terminal. Thus, for example, when the lead wire or the terminal member is pulled in the axial direction (that is, in a direction in which the terminal member is detached), the male-female fitting may become released.

When the male-female fitting becomes released, there is a problem that the electrical connection from the sensor to the circuit board is broken.

The present invention has been made in view of the above-described problem, and an object of the present invention is to provide a terminal member and a connector with which an electrical connection is less likely to be broken even when a lead wire or the like receives external force.

SUMMARY OF THE INVENTION

Means for Solving the Problems (1) A first aspect of the present invention is directed to a long terminal member formed from a metal plate. The terminal member includes: a lead wire connection portion provided at a rear end side and electrically connected to a lead wire; a circuit connection portion provided at a front end side and electrically connected to a circuit board; and an intermediate portion located between the lead wire connection portion and the circuit connection portion. The intermediate portion has a fixing hole penetrating the intermediate portion in a thickness direction and containing an end portion at the front end side of the fixing hole, and an engagement portion projecting in the thickness direction is provided at the end portion of the fixing hole.

In the first aspect, the intermediate portion of the terminal member has the fixing hole, and has, at the end portion at the front end side of the fixing hole, the engagement portion projecting in the thickness direction. Therefore, for example, when the terminal member is attached to a housing, movement of the terminal member (e.g., in a direction in which the lead wire is pulled) can be restricted by fitting a projection portion provided to the housing into the fixing hole.

Furthermore, since the engagement portion is provided in the terminal member, movement of the terminal member (e.g., movement in the direction in which the lead wire is pulled) can be restricted by engaging the engagement portion with an engaged portion such as the surface of the housing, similarly to the projection portion fitted into the fixing hole.

That is, in the first aspect, the terminal member is firmly fixed to the housing by both the fixing hole and the engagement portion, for example, even when great force is applied in the direction in which the lead wire is pulled, movement of the terminal member is assuredly restricted. Therefore, a significant effect is achieved that an electrical connection between the terminal member and the circuit board is less likely to be broken. For example, even in the case where the terminal member is joined to the circuit board by means of soldering, a load is less likely to be applied to the joint portion, and thus the electrical connection can be favorably maintained.

Moreover, in the first aspect, since the terminal member is firmly fixed to the housing as describe above, a possibility of an increase in contact resistance as with contact resistance between a male terminal and a female terminal in the conventional art is low. That is, in the first aspect, for example, loss of signal transmission between a sensor and the circuit board is less likely to occur. Therefore, for example, there is an effect that accuracy of measurement by the sensor is high.

Additionally, in the first aspect, surface treatment (e.g., Au plating, Ag plating, etc.) required for a contact portion between the male terminal and the female terminal in the conventional art can be omitted, and it is also possible to reduce the number of components.

(2) In a second aspect of the present invention, the circuit connection portion has a first bent portion that is bent to a side opposite to a projection direction of the engagement portion, and a second bent portion that is bent to the front end side in a longitudinal direction of the terminal member at the front end side with respect to the first bent portion.

In the second aspect, since the circuit connection portion has both bent portions having the above-described shapes, for example, in the case where a housing is provided with a through hole through which the terminal member is inserted, the terminal member can be assuredly attached to the housing without taking an incorrect orientation (e.g., an incorrect top-bottom orientation in the thickness direction), by forming, for example, a groove corresponding to the shapes of the bent portions, in the through hole.

(3) In a third aspect of the present invention, the circuit connection portion has a third bent portion that is bent in the projection direction of the engagement portion at the front end side with respect to the second bent portion of the circuit connection portion.

In the third aspect, since the front end side of the circuit connection portion is bent in the projection direction of the engagement portion, for example, the circuit connection portion can easily be connected to the circuit board disposed at the projection direction side.

(4) In a fourth aspect of the present invention, the lead wire is connected to the lead wire connection portion.

The fourth aspect indicates an example of a configuration in which the lead wire is connected to the terminal member.

(5) In a fifth aspect of the present invention, an annular seal member is externally fitted on the lead wire.

The fifth aspect indicates an example of a configuration in which the seal member is fitted to the lead wire. Accordingly, when the terminal member is inserted through, for example, a through hole of a housing, the through hole can be sealed (made watertight) by the seal member.

(6) A sixth aspect of the present invention is directed to a connector in which the terminal member according to any one of the first to fifth aspects is attached to a housing having an electrical insulation property.

In the connector, the housing has a through hole penetrating from the lead wire side to the circuit board side, and the terminal member is inserted in the through hole. Furthermore, a front end side of the terminal member projects from an opening at the circuit board side of the through hole, and the engagement portion of the terminal member is engaged with the housing.

In the sixth aspect, the front end side of the terminal member inserted in the through hole of the housing projects from the opening at the circuit board side of the through hole, and the engagement portion of the terminal member is engaged with the housing.

Therefore, the terminal member can be connected at the front end side thereof to the circuit board. In addition, since the engagement portion of the terminal member is engaged with the housing, for example, even when the lead wire is pulled with great force, the terminal member is inhibited from moving in the pulling direction. Therefore, a significant effect is achieved that an electrical connection between the terminal member and the circuit board is less likely to be broken.

Furthermore, in the sixth aspect, since the terminal member is firmly fixed to the housing as described above, for example, even in the case where the terminal member and the circuit board are joined to each other by means of soldering, a load is less likely to be applied to the joint portion. Therefore, also from this point, there is an effect that the electrical connection can be favorably maintained.

Moreover, in the sixth aspect, as described above, the electrical connection is not an electrical connection established through contact between the male terminal and the female terminal. Thus, contact resistance is less likely to increase, and loss of signal transmission is less likely to occur. Therefore, for example, there is an effect that accuracy of measurement by a sensor is high.

Additionally, in the sixth aspect, the above-described surface treatment can be omitted, and it is also possible to reduce the number of components.

(7) A seventh aspect of the present invention is directed to a connector in which the terminal member according to the fourth aspect or the fifth aspect is attached to a housing having an electrical insulation property.

In the connector, the housing has a through hole penetrating from the lead wire side to the circuit board side, the terminal member is inserted in the through hole, and the housing has a surface provided along the intermediate portion of the terminal member inserted in the through hole, the surface opposing the intermediate portion. Furthermore, a front end side of the terminal member projects from an opening at the circuit board side of the through hole, and the engagement portion of the terminal member is engaged with the housing. Moreover, the surface opposing the intermediate portion is provided so as to extend at a radially outer side with respect to an axial center of a lead wire insertion hole at a side at which the lead wire is inserted, of the through hole, and at least a base portion projecting from the intermediate portion, of the engagement portion, is disposed at a side at which the surface extends, with respect to the axial center of the lead wire insertion hole.

The seventh aspect achieves the same advantageous effects as those of the sixth aspect.

In addition, in the seventh aspect, the surface of the housing opposing the intermediate portion of the terminal member extends at the radially outer side with respect to the axial center of the lead wire insertion hole, and the base portion of the engagement portion of the terminal member is disposed at the side at which the surface extends, with respect to the axial center of the lead wire insertion hole. Therefore, for example, there is an effect that even when the lead wire is pulled to the outside of the housing with great force, the engagement of the terminal member is less likely to be released.

Hereinafter, the reason for this will be described.

Since the lead wire is disposed along the axial center of the lead wire insertion hole, when the lead wire is pulled with great force, the terminal member connected to the lead wire is also pulled along the axial center.

However, in the seventh aspect, for example, as shown in FIG. 18B described later, the base portion of the engagement portion is disposed in the direction in which the surface extends (at the upper side in FIG. 18B) with respect to the axial center of the lead wire insertion hole. Therefore, when the lead wire is pulled, the pulling force is applied in a direction of a portion (e.g., Q in FIG. 18C) at which the lead wire is connected (e.g., in the direction of an arrow P) in the base portion. Thus, in the base portion, components of the pulling force are applied not only in a direction along the axial center (e.g., an X direction) but also in a direction perpendicular to the direction along the axial center (e.g., a Y direction).

The perpendicular direction is a direction that is a direction toward the axial center and is opposite to the direction in which the surface extends (i.e., the direction in which the engagement portion is disengaged). Thus, the engagement portion receives force toward the axial center side and becomes less likely to be disengaged from the housing.

As described above, in the seventh aspect, a significant effect is achieved that when the lead wire is pulled, the terminal member becomes less likely to drop off from the housing due to the component of the force toward the axial center side.

(8) In an eighth aspect of the present invention, the housing includes a projection portion that is fitted in the fixing hole of the terminal member, and an engaged portion with which the engagement portion of the terminal member is engaged.

In the eighth aspect, when the terminal member is attached to the housing, movement of the terminal member (e.g., in the direction in which the lead wire is pulled) can be restricted by fitting the projection portion of the housing into the fixing hole. Furthermore, movement of the terminal member (e.g., movement in the direction in which the lead wire is pulled) can be restricted, similarly to the above, by engaging the engagement portion of the terminal member with the engaged portion of the housing.

That is, in the eighth aspect, the terminal member is firmly fixed to the housing by both the fixing hole and the engagement portion, and thus movement of the terminal member is assuredly inhibited, for example, even when great force is applied in the direction in which the lead wire is pulled.

Therefore, a significant effect is achieved that the electrical connection between the terminal member and the circuit board is less likely to be broken. For example, even in the case where the terminal member is joined to the circuit board by means of soldering, a load is less likely to be applied to the joint portion, and thus the electrical connection can be favorably maintained.

(9) In a ninth aspect of the present invention, movement of the terminal member toward the rear end side is restricted by the projection portion being engaged with the end portion at the front end side of the fixing hole of the terminal member.

The ninth aspect indicates an example of a direction in which movement of the terminal member is restricted by the projection portion.

(10) In a tenth aspect of the present invention, movement of the terminal member toward the rear end side is restricted by the engagement portion being engaged with the engaged portion of the housing.

The tenth aspect indicates an example of a direction in which movement of the terminal member is restricted by the engagement portion.

(11) In an eleventh aspect of the present invention, the circuit connection portion has a first bent portion that is bent to a side opposite to a projection direction of the engagement portion, and a second bent portion that is bent to the front end side in a longitudinal direction of the terminal member at the front end side with respect to the first bent portion, and the through hole of the housing includes a groove that allows a portion of the terminal member between the first bent portion and the second bent portion to pass therethrough and is provided along a penetration direction of the through hole and at a position opposite to a position at which the projection portion is disposed.

In the eleventh aspect, since the circuit connection portion has a structure in which the circuit connection portion is bent at the first bent portion and the second bent portion, in the case of inserting the terminal member through the through hole of the housing, the terminal member can be assuredly attached to the housing without taking an incorrect orientation (top-bottom orientation in the thickness direction), by passing a portion between the first bent portion and the second bent portion (i.e., the portion bent relative to the longitudinal direction of the terminal member) through the groove of the through hole.

(12) In a twelfth aspect of the present invention, a width of the intermediate portion in the terminal member is larger than a width of the circuit connection portion and a width of the groove of the through hole, and the width of the circuit connection portion is smaller than the width of the groove of the through hole.

In the twelfth aspect, by passing the circuit connection portion having a smaller width than the intermediate portion through the groove of the through hole having a smaller width than the intermediate portion, the top-bottom orientation of the through hole (i.e., the orientation in the thickness direction) can coincide with the top-bottom orientation of the terminal member. Thus, the terminal member can be assembled into the through hole without taking an incorrect top-bottom orientation.

(13) In a thirteenth aspect of the present invention, the housing has a protrusion portion projecting toward the circuit board side, and a part of a surface of the protrusion portion and a part of an inner peripheral surface of the through hole have the same flat surface.

In the thirteenth aspect, since the surface of the protrusion portion and the inner peripheral surface of the through hole have the same flat surface, the plate-like intermediate portion of the terminal member can be disposed on the same flat surface.

(14) In a fourteenth aspect of the present invention, the projection portion is provided on the part of the surface of the protrusion portion that is the same flat surface.

In the fourteenth aspect, since the projection portion is provided on the surface of the protrusion portion provided outside the through hole, the height of the projection portion is not restricted by the height of the through hole and can be set to a preferable height (a height at which the projection portion is easily fitted into the fixing hole and is less likely to be detached therefrom).

(15) In a fifteenth aspect of the present invention, a distance from the same flat surface to both step portions forming both sides in a width direction of the groove of the through hole of the housing is equal to or less than a distance from the same flat surface to the projection portion.

In the fifteenth aspect, since the distance from the same flat surface to both step portions in the width direction of the groove of the through hole (i.e., portions at which both edges in the width direction of the intermediate portion of the terminal member are disposed) is equal to or less than the distance from the same flat surface to the projection portion, when the projection portion is fitted in the fixing hole of the terminal member, the terminal member is restricted by both step portions of the groove and is less likely to move in the thickness direction of the terminal member (i.e., the direction in which the projection portion projects). Thus, there is an advantage that the terminal member is less likely to drop off from the housing.

(16) In a sixteenth aspect of the present invention, the through hole of the housing is sealed by a seal member externally fitted on the lead wire.

In the sixteenth aspect, the through hole can be suitably sealed (made watertight) by the above-described seal member.

<Hereinafter, each component of the present invention will be described.>

The terminal member is a metallic member having electrical conductivity, and as the material of the terminal member, for example, a copper alloy (e.g., brass (Cu—Zn based), phosphor bronze (Cu—Sn—P based), beryllium copper (Cu—Be based), Corson copper (Cu—Ni—Si based)), or the like can be adopted.

As the lead wire, signal wires connected to various sensor can be adopted.

The housing is a member having an electrical insulation property, a resin, etc. can be adopted as the material of the housing, and, for example, a crystalline resin (e.g., polyamide (PA), polybutylene terephthalate (PBT), polyphenylene sulfide (PPS)), or the like can be adopted as the resin.

As the seal member, for example, a rubber having elasticity such as silicone can be adopted.

BRIEF DESCRIPTION OF THE DRAWINGS

These and other features and advantages of the present invention will become more readily appreciated when considered in connection with the following detailed description and appended drawings, wherein like designations denote like elements in the various views, and wherein:

FIG. 5B is a perspective view showing a lower surface side of the housing.

DETAILED DESCRIPTION OF THE INVENTION

Next, embodiments of a terminal member and a connector of the present invention will be described.

1. First Embodiment

[1-1. Entire Configuration]

First, the entire configuration of a system regarding a sensor device including a connector will be described.

Figure 1:
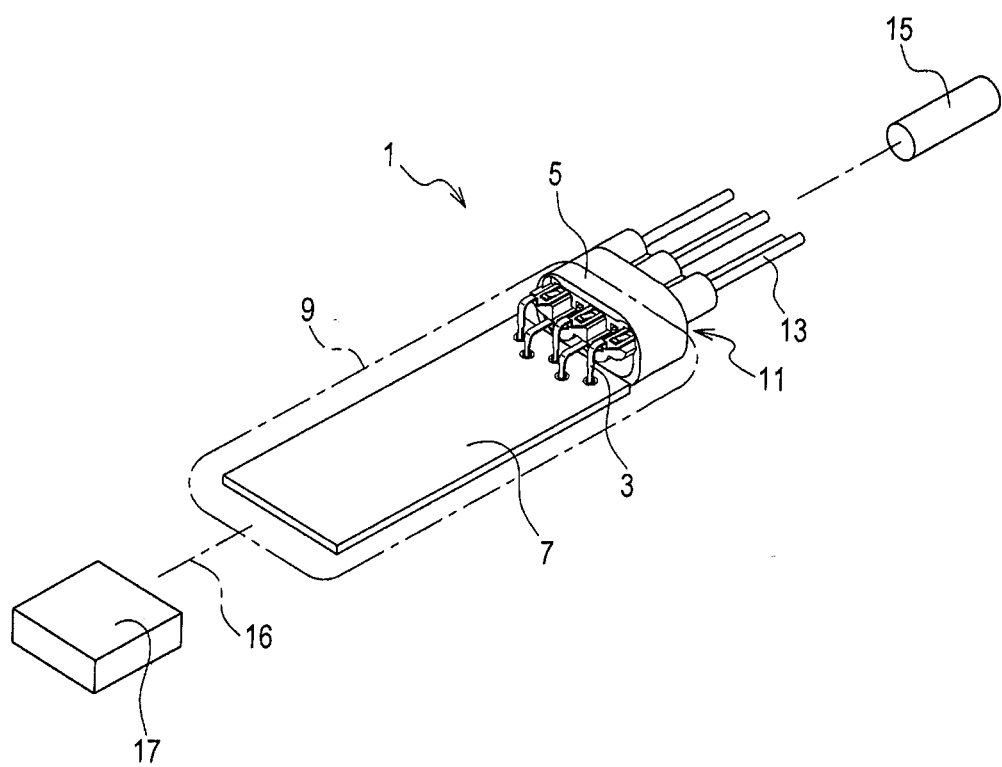
FIG. 1 is an explanatory diagram schematically showing the entire configuration of a system including a sensor device of a first embodiment.
Figure 2A:
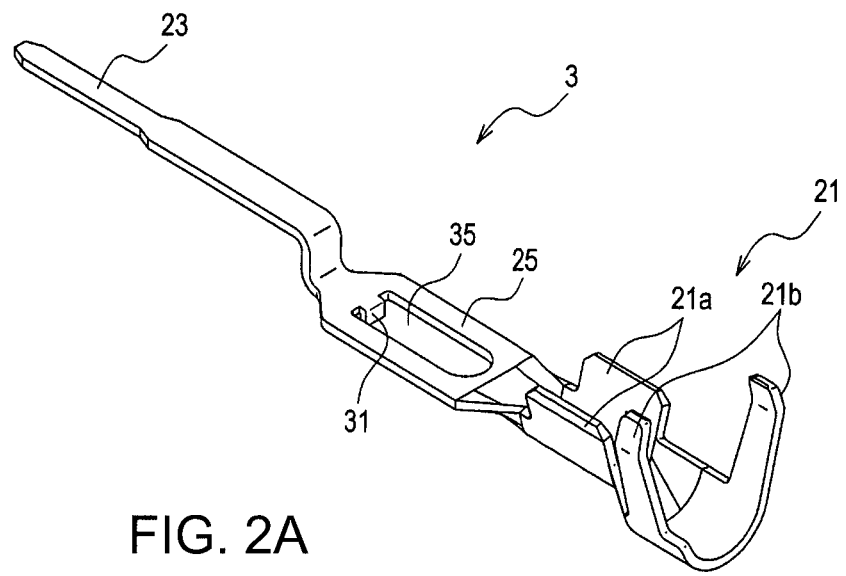
FIGS. 2A and 2B are perspective views showing a terminal member to which a lead wire is not connected.
Figure 2B:
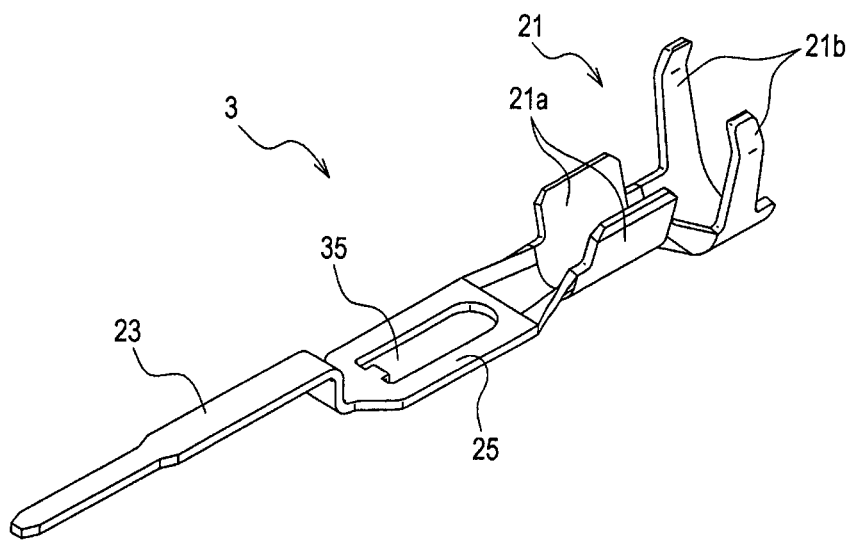

As shown in FIG. 1, a sensor device 1 includes a plurality of terminal members 3, a housing 5 to which the plurality of terminal members 3 are attached, a circuit board 7 that is electrically connected to the plurality of terminal members 3, and a container 9 that houses these components. A member in which the terminal members 3 are attached to the housing 5 is referred to as connector 11.

A sensor 15 is connected to the plurality of terminal members 3 via lead wires 13 that are signal wires, respectively, and the circuit board 7 is connected to an electronic control device 17 via an external terminal (not shown) and an external cable 16.

The sensor 15 is, for example, an oxygen sensor that is provided on an exhaust pipe of an internal combustion engine and detects the concentration of oxygen in exhaust gas.

Specifically, although not shown, the sensor 15 has a known configuration in which, for example, a gas sensor element is housed in a housing. The gas sensor element is a plate-like element in which an oxygen pump cell and an oxygen concentration detection cell each having a pair of electrodes formed on the surface of a solid electrolyte and a heater for heating these cells are stacked.

In addition, the circuit board 7 of the sensor device 1 performs drive control on the sensor 15 and outputs an electric signal based on a result of detection by the sensor 15, to the electronic control device 17.

Specifically, the circuit board 7 having circuit components mounted thereon controls the magnitude and the flow direction of a current to be applied to the oxygen pump cell such that a voltage between the electrodes of the oxygen concentration detection cell in the gas sensor element of the sensor 15 has a constant value. In addition, the circuit board 7 detects the concentration of oxygen in the exhaust gas by detecting a current flowing through the oxygen pump cell via a detection resistor, and outputs an electric signal indicating information regarding the concentration of oxygen, to the electronic control device 17.

Hereinafter, each component, etc. will be described.

[1-2. Terminal Members]

First, the terminal members 3 will be described.

As shown in FIGS. 2A-2B and FIGS. 3A-3B, each terminal member 3 is a long member obtained by processing a metal plate formed from a copper alloy (e.g., phosphor bronze). FIGS. 2A-2B and FIGS. 3A-3B show a state before the lead wire 13 is connected.

The terminal member 3 includes, at a rear end side thereof (the right side in FIG. 3A), a lead wire connection portion 21 to be connected to the lead wire 13, includes, at a front end side thereof (the left side in FIG. 3A), a circuit connection portion 23 to be connected to the circuit board 7, and further includes a plate-like intermediate portion 25 between the lead wire connection portion 21 and the circuit connection portion 23.

The lead wire connection portion 21 includes a pair of core wire connection portions 21a disposed at the front end side, and a pair of substantially annular seal member holding portions 21b disposed at the rear end side.

Among these portions, the core wire connection portions 21a serve to fix (i.e., crimp) a core wire 13a (see FIG. 4A) of the lead wire 13, and are formed at both edges in a width direction of the terminal member 3 (the up-down direction in FIG. 3A) so as to project in the width direction and one direction in the vertical direction (the upward direction in FIG. 3B: hereinafter, this direction is referred to as upward).

Meanwhile, the seal member holding portions 21b serve to hold a seal member 27 (see FIG. 4A), and are formed at the rear end side with respect to the core wire connection portions 21a so as to project upward from both edges in the width direction.

Figure 3A:
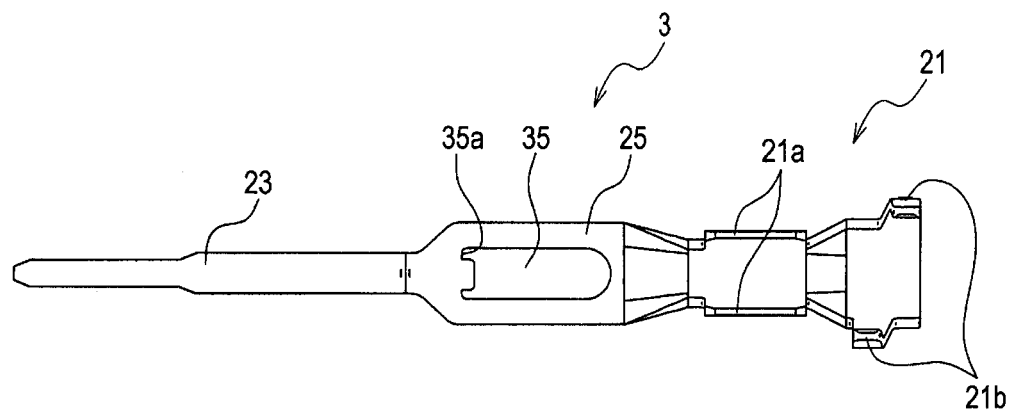
FIG. 3A is a plan view of the terminal member to which the lead wire is not connected.
Figure 3B:
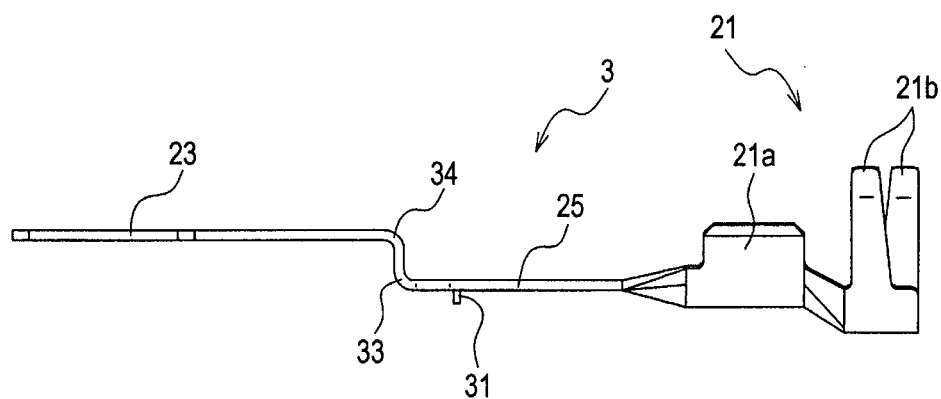
FIG. 3B is a front view of the terminal member.

A range from the rear end side with respect to the intermediate portion 25 to the rear end of the lead wire connection portion 21 is curved so as to be convex toward a radially outer side at the lower side in FIG. 3B such that the axial centers of the lead wire 13 and the seal member 27 and a position along the surface of the intermediate portion 25 coincide with each other.

Figure 4A:
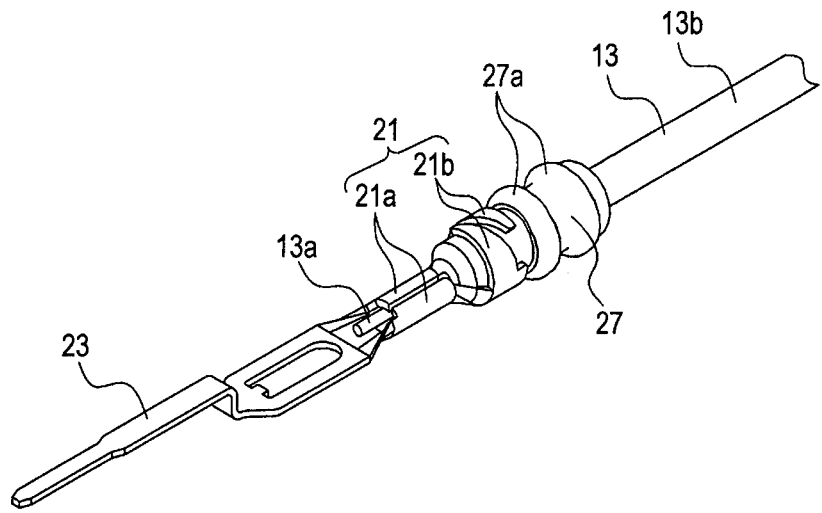
FIG. 4A is a perspective view showing an upper surface side of the terminal member to which the lead wire is connected.
Figure 4B:
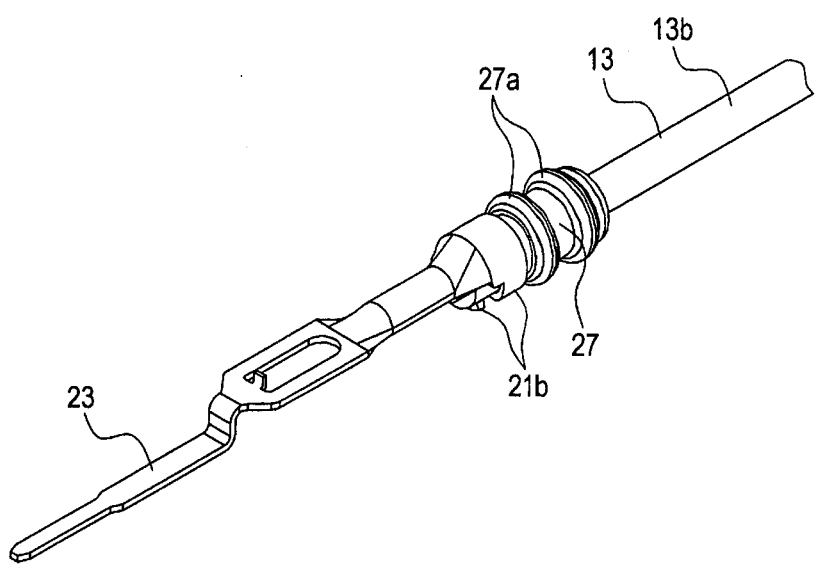
FIG. 4B is a perspective view showing a lower surface side of the terminal member (a side at which an engagement portion projects).

As shown in FIGS. 4A-4B, the lead wire 13 is connected to the lead wire connection portion 21, and the lead wire 13 is obtained by coating the outer periphery of the core wire 13a having electrical conductivity with a coating portion 13b having an electrical insulation property.

Specifically, the core wire connection portions 21a are bent so as to surround the outer periphery of the core wire 13a to crimp the core wire 13a, whereby the terminal member 3 and the core wire 13a (therefore, the lead wire 13) are integrally fixed and electrically connected to each other.

In addition, the seal member 27 having an annular shape (i.e., a cylindrical shape) is externally fitted on the coating portion 13b of the lead wire 13. The seal member holding portions 21b are bent at the front end side of the seal member 27 so as to surround the outer periphery of the seal member 27 and hold the seal member 27 in a state of pressing the seal member 27.

The seal member 27 is, for example, a rubber member having elasticity and formed from silicone. An annular projection portion 27a having a larger diameter than a portion of the seal member 27 held by the seal member holding portions 21b is provided at the rear end side of the seal member 27, and the terminal member 3 is held to the housing 5 and also the outer peripheral side of the seal member 27 is sealed (made watertight) by the annular projection portion 27a as described later.

Meanwhile, as shown in FIG. 3B, the circuit connection portion 23 has a shape in which a long plate is bent at two locations.

That is, the circuit connection portion 23 has a first bent portion 33 that is bent from the intermediate portion 25 to the side (the upper side) opposite to the projection direction of an engagement portion 31 described later (the lower side in FIG. 3B), and a second bent portion 34 that is bent to the front end side in the longitudinal direction of the terminal member 3 (in the right-left direction in FIG. 3A) at the front end side with respect to the first bent portion 33.

As shown in FIG. 3A, the width of the circuit connection portion 23 is set so as to be smaller than the width of the intermediate portion 25.

Figure 5A:
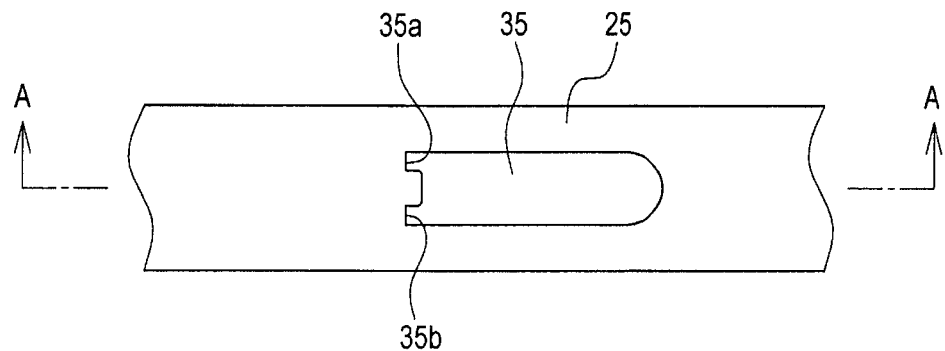
FIG. 5A is a plan view showing a part of an intermediate portion of the terminal member.
Figure 5B:
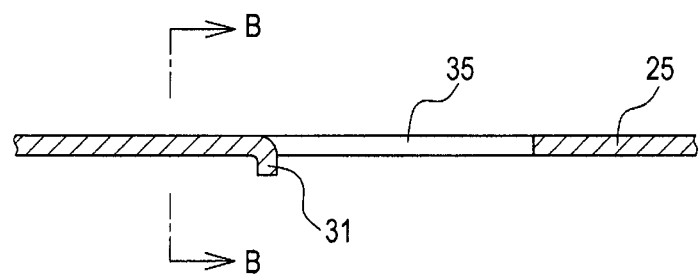
FIG. 5B is an A-A cross-sectional view of FIG. 5A.

In addition, as shown in FIG. 5, the intermediate portion 25 has a fixing hole 35 that penetrates the intermediate portion 25 in the thickness direction of the intermediate portion 25, and also has, at an end portion 35a at the front end side of the fixing hole 35, the engagement portion 31 projecting toward the lower side in the thickness direction (the lower side in FIG. 5B).

Figure 5C:
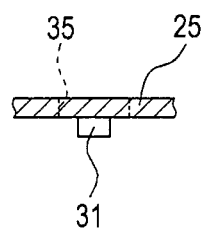
FIG. 5C is a B-B cross-sectional view of FIG. 5B.

Specifically, the fixing hole 35 is a long hole that is long in the longitudinal direction, and the engagement portion 31 that has a width shorter than the width of the end portion 35a (therefore, the width of the fixing hole 35: the dimension in the up-down direction in FIG. 5A) projects at a part of the end portion 35a at the front end side of the fixing hole 35 downward and perpendicularly relative to the intermediate portion 25 as shown in FIG. 5C.

The engagement portion 31 is a rectangular plate, and the height thereof (i.e., the dimension by which the engagement portion 31 projects from the lower surface of the intermediate portion 25) is, for example, equal to or greater than the thickness of the intermediate portion 25.

[1-3. Housing]

Next, the housing 5 to which the terminal members 3 are attached will be described.

Figure 6A:
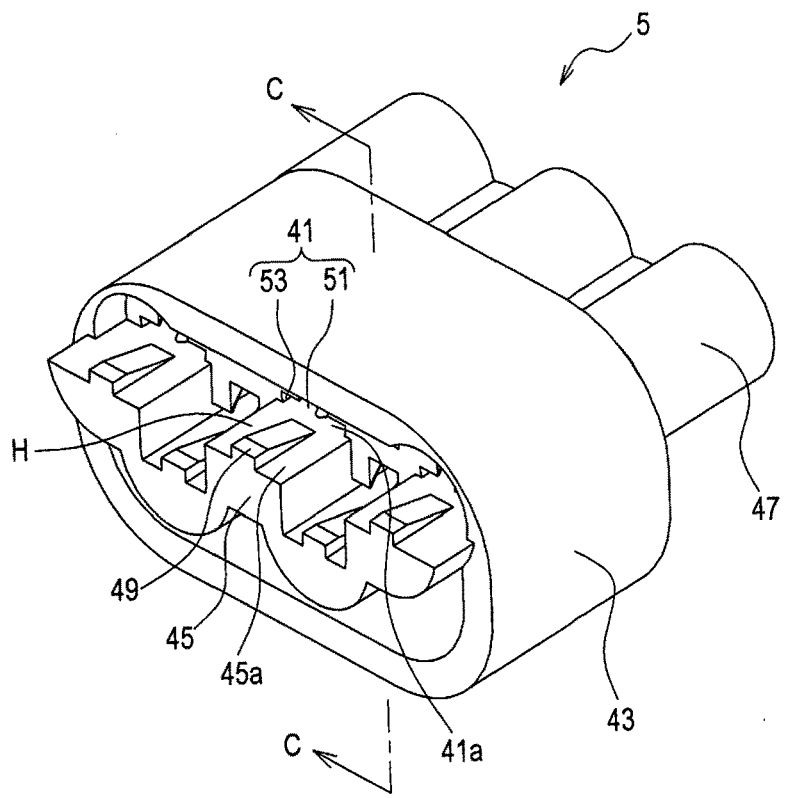
FIG. 6A is a perspective view showing an upper surface side of a housing (a side at which a projection portion is formed)
Figure 6B:
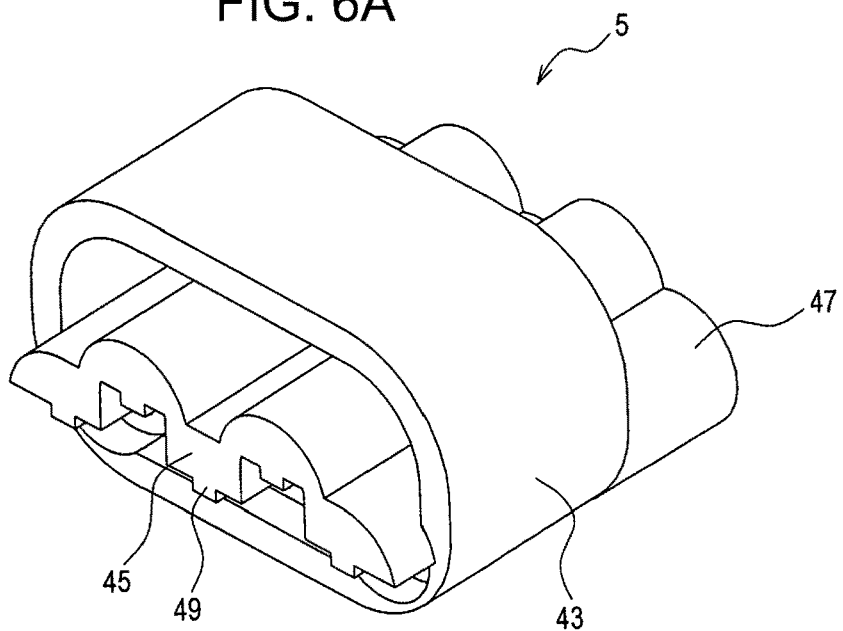
Figure 7A:
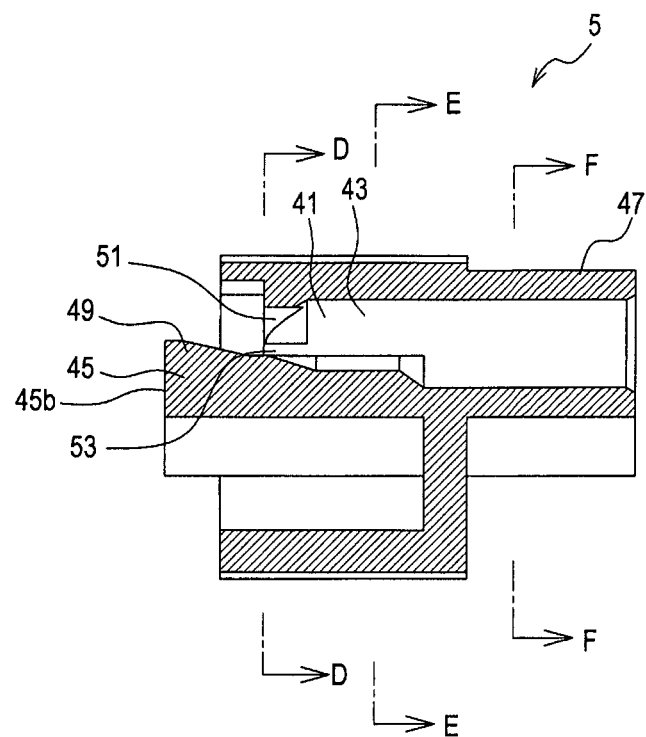
FIG. 7A is a C-C cross-sectional view of FIG. 6A.

As shown in FIGS. 6A-6B and FIGS. 7A-7B, the housing 5 is a tubular member formed from a resin having an electrical insulation property (e.g., polyamide), and a plurality of (here, five) through holes 41 through which the plurality of (here, five) terminal members 3 are inserted are formed so as to penetrate the housing 5 in an axial direction (penetration direction: the right-left direction in FIG. 7A).

Specifically, the housing 5 includes a tubular center portion 43, a protrusion portion 45 that projects from the center portion 43 toward a front end side (the left side in FIG. 7A), and a tubular seal portion 47 that projects from the center portion 43 toward a rear end side.

Figure 7B:
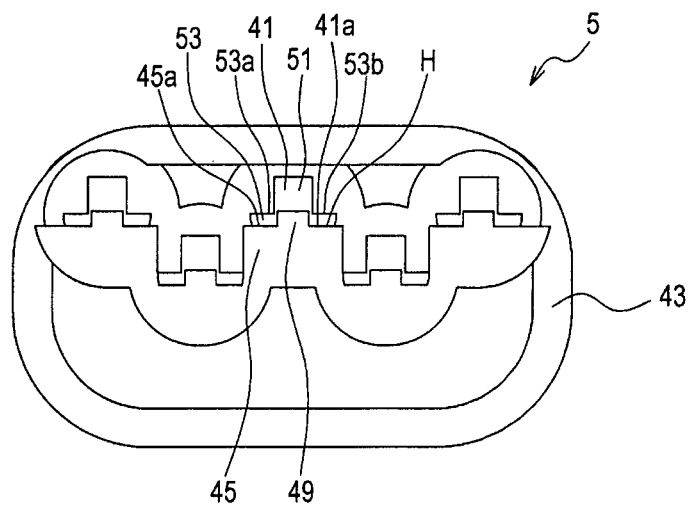
FIG. 7B is a left side view of the housing.

Among these portions, in the center portion 43, the above-described through holes 41 are provided so as to reach the tubular seal portion 47. As shown in FIG. 7B, three of the five through holes 41 are aligned in one row in the right-left direction in FIG. 7B in an upper portion of the center portion 43, and the remaining two are aligned in one row in the right-left direction in FIG. 7B in a lower portion of the center portion 43.

As shown in FIG. 7B, an opening portion at the front end side of each through hole 41 has a cross-section that is perpendicular to the penetration direction of the through hole 41 and that has a projection shape in which a upper portion is narrower in width stepwise than a lower portion.

Specifically, a groove 51 is formed at an upper portion of the through hole 41, that is, at a position at the side opposite to (above) the position at which a later-described projection portion 49 is disposed. The groove 51 has a cross-sectional shape that allows a portion between the first bent portion 33 and the second bent portion 34 to pass therethrough when the terminal member 3 is passed through the through hole 41 along the penetration direction of the through hole 41.

The dimension in the width direction (the right-left direction in FIG. 7B) of the groove 51 is longer than the dimension in the width direction of the circuit connection portion 23 of the terminal member 3 and shorter than the dimension in the width direction of the intermediate portion 25.

Figure 8A:
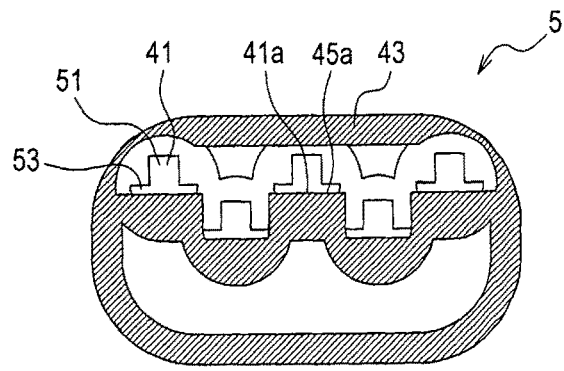
FIG. 8A is a D-D cross-sectional view of FIG. 7A.

In addition, a portion of each through hole 41 below the groove 51 at the upper portion is a wide portion 53 having a rectangular (cross-sectional) shape in which the dimension in the width direction is longer than that of the groove 51 (see FIG. 8A). The dimension in the up-down direction of the wide portion 53 is slightly longer than the dimension in the thickness direction of the intermediate portion 25.

Furthermore, as shown in FIG. 6A, an upper surface 45a of the protrusion portion 45 that projects from each through hole 41 toward the front end side (i.e., the surface at the upper side in FIG. 7B) and a part of a lower surface 41a of each through hole 41 form the same flat surface H, and the projection portion 49 that projects upward (i.e., upward in FIG. 7B) is formed on the upper surface 45a of the protrusion portion 45 (which is the same flat surface H).

As shown in FIG. 7B, the projection portion 49 is provided at the center in the width direction of the upper surface 45a of the protrusion portion 45 such that the center thereof coincides with the center in the width direction of the through hole 41. That is, the position and the dimension in the width direction of the projection portion 49 are set according to the position and the shape of the fixing hole 35 such that, when the terminal member 3 is inserted through the through hole 41, the projection portion 49 is fitted into the fixing hole 35 of the terminal member 3.

In addition, the width of the projection portion 49 is slightly smaller than the width of the groove 51. Furthermore, the distance from the same flat surface H to both step portions 53a and 53b that form both sides in the width direction of the groove 51 of the through hole 41 is equal to or less than the distance from the same flat surface H to the projection portion 49.

The shape of the projection portion 49 from the front end side to the rear end side (i.e., in the longitudinal direction) is higher at the front end side, and is lower toward the rear end side, as shown in FIG. 7A. The front end of the projection portion 49 forms the same flat surface as a front end surface 45b of the protrusion portion 45 (a flat surface perpendicular to the longitudinal direction), and the front end surface 45b of the protrusion portion 45 is an engaged portion with which the engagement portion 31 of the terminal member 3 is engaged.

Furthermore, the tubular seal portion 47 is a portion into which the seal member 27 through which the lead wire 13 is inserted and held. As shown in FIG. 8C, the tubular seal portion 47 has, as parts of the through holes 41, lead wire insertion holes 42 into each of which the seal member 27 is inserted, and the cross-sectional shape of each lead wire insertion hole 42 is formed as a circular column shape according to the outer periphery of the seal member 27.

Figure 8B:
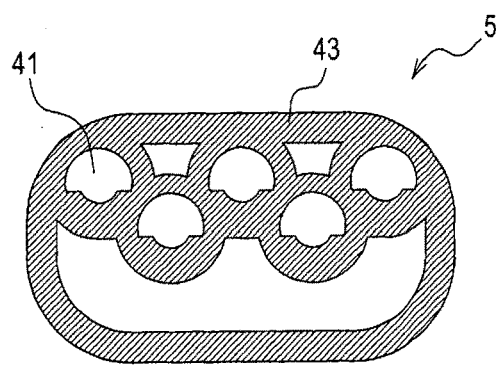
FIG. 8B is an E-E cross-sectional view of FIG. 7A.
Figure 8C:
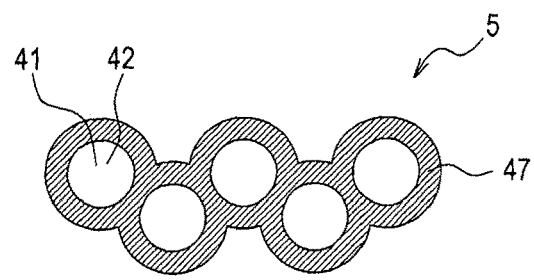
FIG. 8C is an F-F cross-sectional view of FIG. 7A.
Figure 9A:
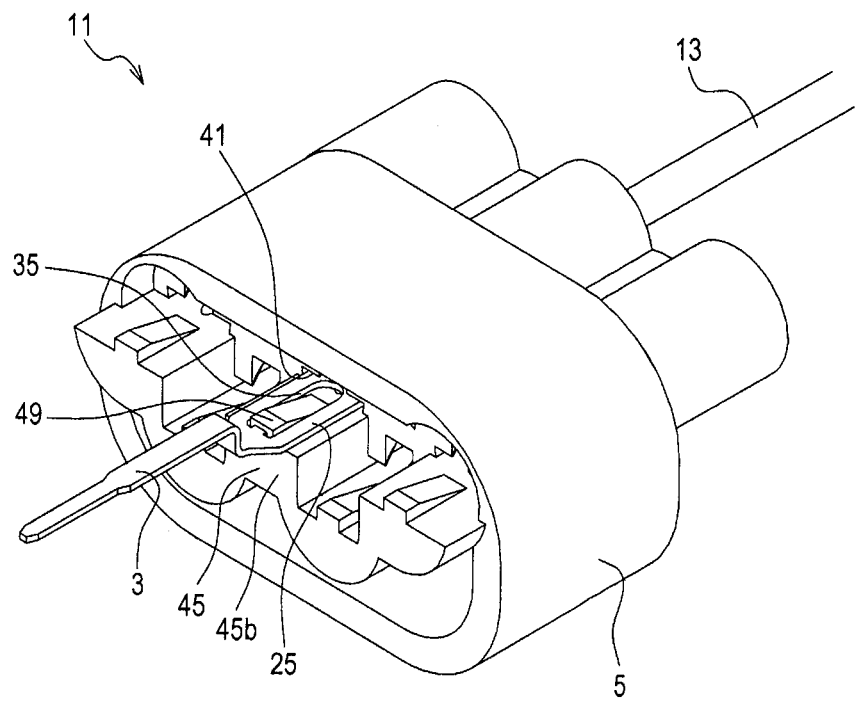
FIG. 9A is a perspective view showing an upper surface side of a connector (to which one terminal member is attached) of the first embodiment.
Figure 9B:
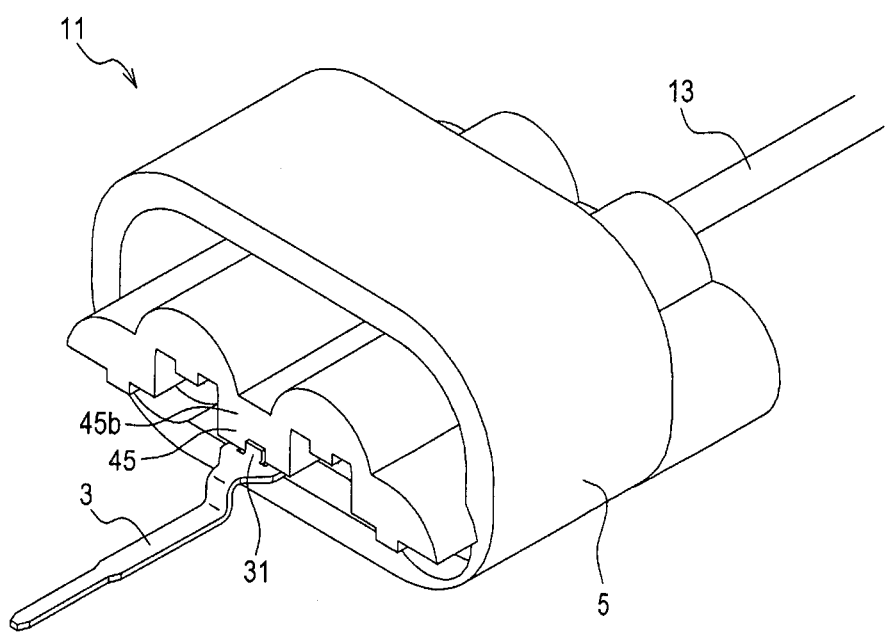
FIG. 9B is a perspective view of a lower surface side of the connector.

The shape of the through hole 41 from the opening end at the front end side to the tubular seal portion 47 is a shape along the outer shape of the terminal member 3, for example, as shown in FIG. 8B.

[1-4. Connector]

Next, the connector 11 in which the terminal members 3 are fixed to the housing 5 will be described.

As shown in FIGS. 9A-9B and FIGS. 10A-10C, the connector 11 is a member in which the terminal members 3 are inserted and fixed through the through holes 41 of the housing 5.

Figure 10A:
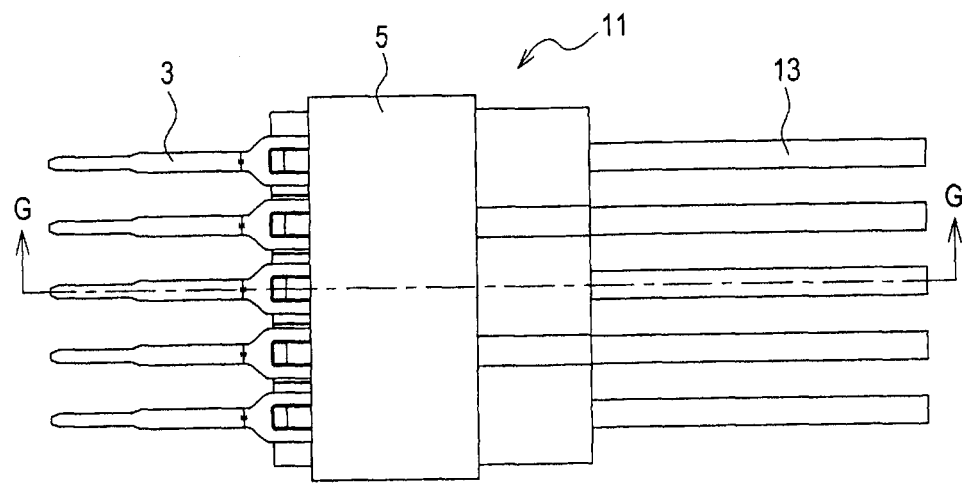
FIG. 10A is a plan view showing the connector (to which five terminal members are attached)
Figure 10B:
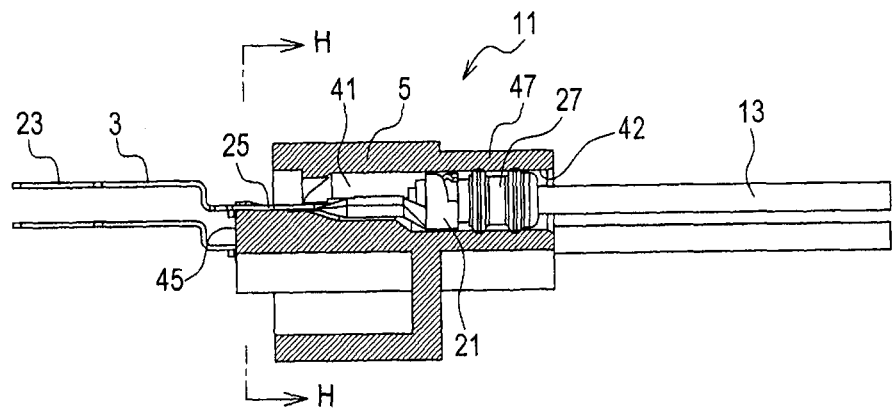
FIG. 10B is a G-G cross-sectional view of FIG. 10A.
Figure 10C:
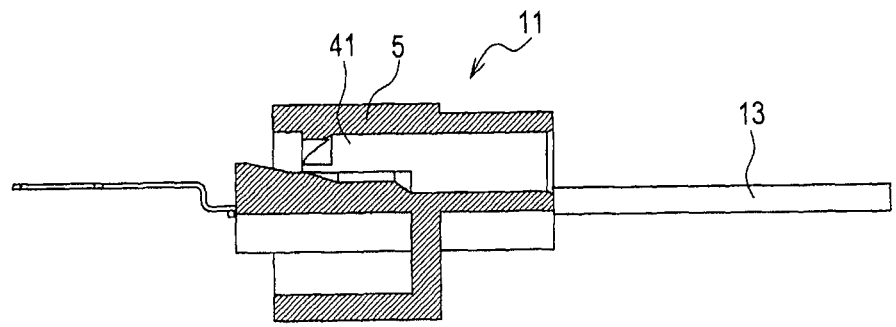
FIG. 10C is a cross-sectional view showing a state where a part of the terminal members are removed from the G-G cross-section of FIG. 10B.

As shown in FIG. 10B, the lead wire 13 and the seal member 27 are connected to each terminal member 3 at the rear end side thereof. The range of the terminal member 3 from the rear end side of the intermediate portion 25 to the lead wire connection portion 21 is disposed in the through hole 41, and the range of the terminal member 3 from a substantially center portion of the intermediate portion 25 to the circuit connection portion 23 projects at the front end side with respect to the through hole 41. The circuit connection portion 23 projects at the front end side with respect to the protrusion portion 45.

In addition, the seal member 27 held at the rear end side of the terminal member 3 is press-fitted and held in the through hole 41 in the tubular seal portion 47 (i.e., the lead wire insertion hole 42). The through hole 41 is sealed (made watertight) by the seal member 27.

Figure 11A:
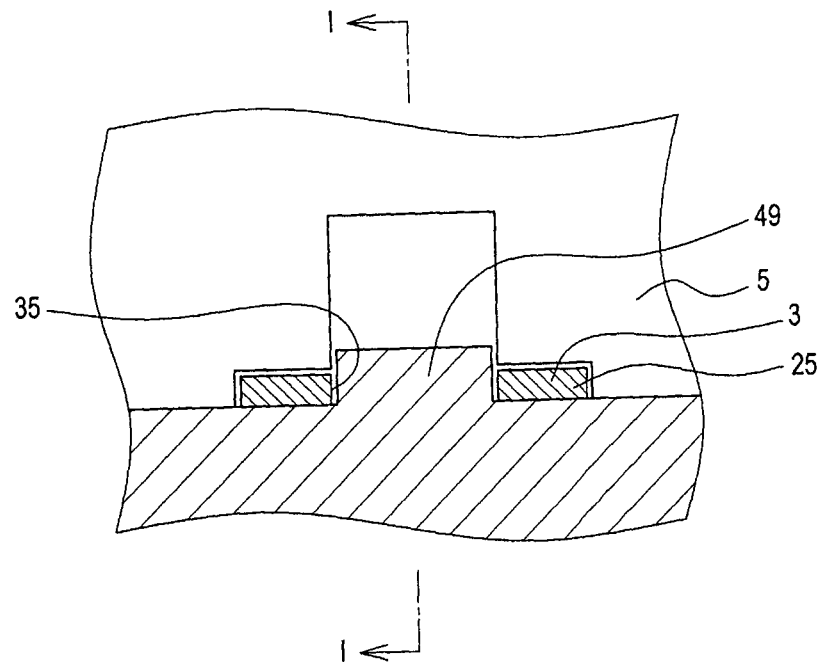
FIG. 11A is a cross-sectional view showing an H-H cross-section of FIG. 10A in an enlarged manner.
Figure 11B:
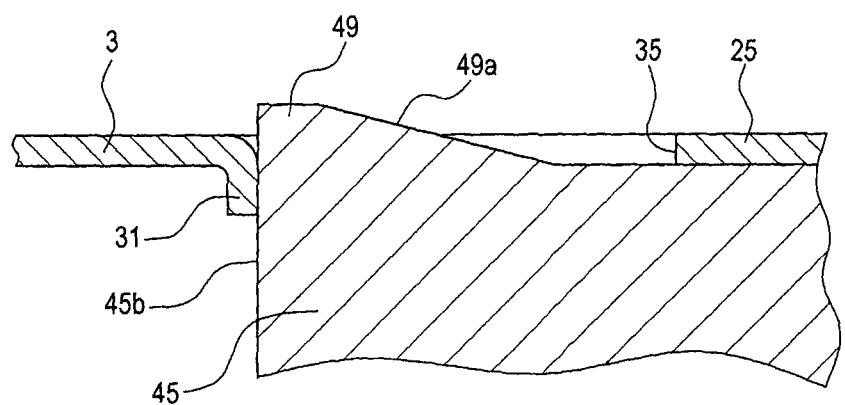
FIG. 11B is an I-I cross-sectional view of FIG. 11A.

Furthermore, as shown in FIGS. 11A and 11B in an enlarged manner, the projection portion 49 of the housing 5 is fitted in the fixing hole 35 of the intermediate portion 25 of the terminal member 3, and the engagement portion 31 of the intermediate portion 25 is engaged with the front end surface 45b of the protrusion portion 45.

[1-5. Assembling Method for Connector]

Next, an assembling method for the connector 11 will be described.

Figure 12A:
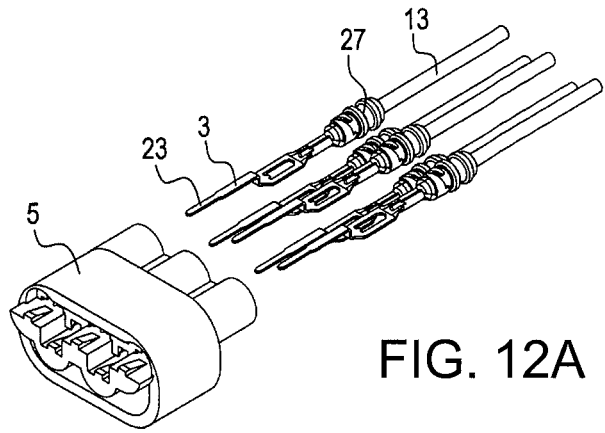
FIGS. 12A-12D are explanatory diagrams illustrating an assembling method for the connector when the upper surface side of the connector is seen from an oblique direction.
Figure 13A:
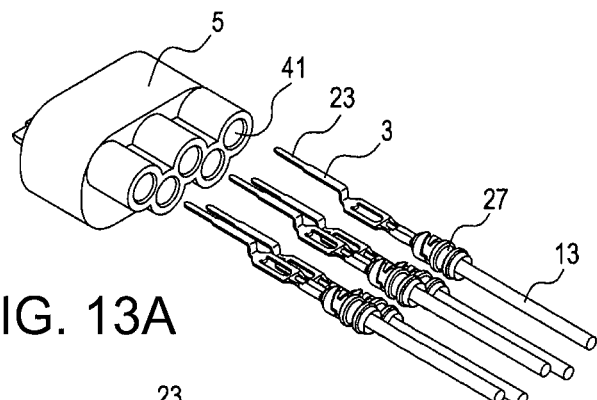
FIGS. 13A-13D are explanatory diagrams illustrating the assembling method for the connector when the lower surface side of the connector is seen from an oblique direction.

As shown in FIG. 12A and FIG. 13A, first, the terminal members 3 to which the lead wires 13 and the seal members 27 are connected are inserted into the through holes 41 from the rear end side of the housing 5 such that the circuit connection portions 23 enters thereinto first.

Figure 12B:
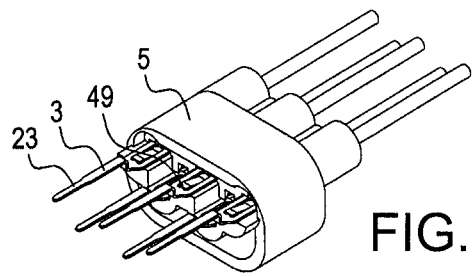
Figure 13B:
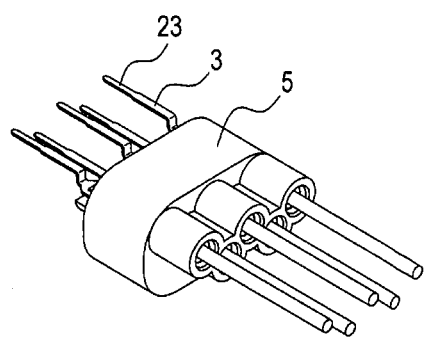

Next, as shown in FIG. 12B and FIG. 13B, the seal member 27 of each terminal member 3 is press-fitted into the through hole 41 (specifically, the lead wire insertion hole 42) such that the circuit connection portion 23 of the terminal member 3 projects at the front end side with respect to the through hole 41 of the housing 5. At this time, the outer peripheral portion of the annular projection portion 27a of the seal member 27 and the inner peripheral portion of the lead wire insertion hole 42 are brought into close contact with each other (see FIG. 10B).

Accordingly, as shown in FIG. 11B, the projection portion 49 of the housing 5 is fitted into the fixing hole 35 of the intermediate portion 25 of the terminal member 3, and the front end side of the intermediate portion 25 of the terminal member 3 comes into contact with an inclined portion 49a at the rear end side of the projection portion 49 and bends upward, so that the engagement portion 31 climbs over the projection portion 49 and comes into contact with the front end surface 45b of the protrusion portion 45.

Figure 12C:
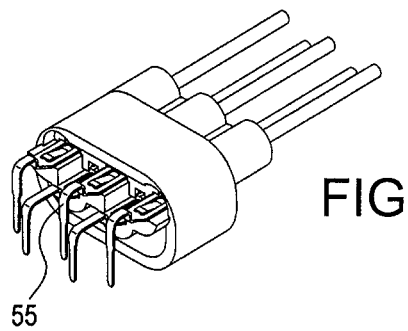
Figure 13C:
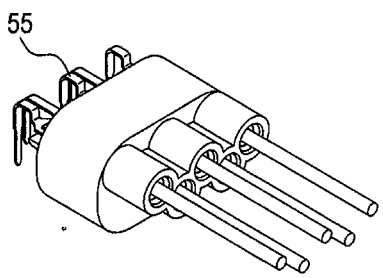

Next, as shown in FIG. 12C and FIG. 13C, the circuit connection portion 23 of each terminal member 3 is perpendicularly bent at the front end side with respect to the second bent portion 34 (i.e., at a third bent portion 55) and in the projection direction of the engagement portion 31 (to the circuit board 7 side).

Figure 12D:
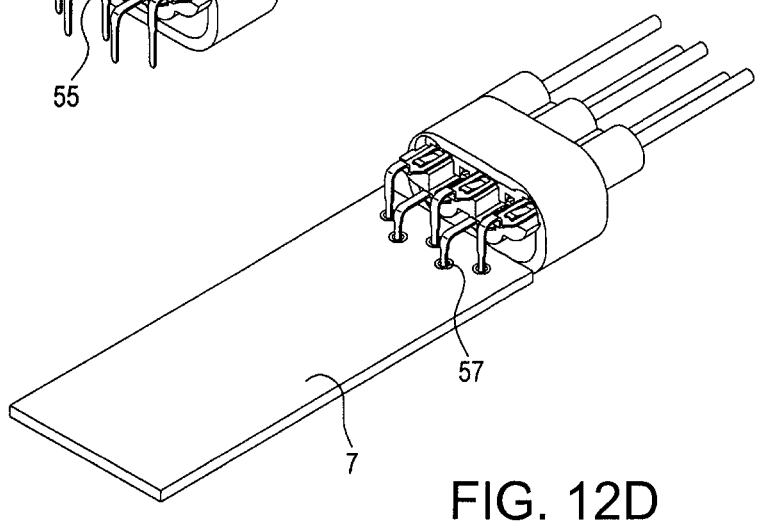
Figure 13D:
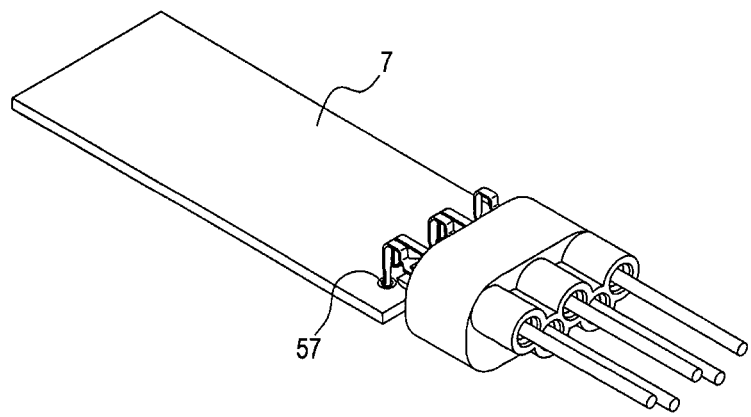

Next, as shown in FIG. 12D and FIG. 13D, the front end side of each circuit connection portion 23 with respect to the third bent portion 55 is inserted into a connection hole 57 of the circuit board 7, and the circuit connection portion 23 of each terminal member 3 is joined and integrally fixed to the circuit board 7, for example, by means of soldering.

[1-6. Advantageous Effects]

Next, advantageous effects of the first embodiment will be described.

(1) In the first embodiment, the intermediate portion 25 of each terminal member 3 has the fixing hole 35, and the engagement portion 31 projecting downward in the thickness direction is provided at the end portion 35a at the front end side of the fixing hole 35. Therefore, when the terminal member 3 is attached to the housing 5, movement of the terminal member 3 toward the rear end side can be restricted by fitting the projection portion 49 of the housing 5 into the fixing hole 35.

Furthermore, since the engagement portion 31 is provided to the terminal member 3, movement of the terminal member 3 toward the rear end side can be restricted, similarly to the above, by engaging the engagement portion 31 with the front end surface (engaged portion) 45b of the protrusion portion 45 of the housing 5.

That is, in the first embodiment, since the terminal member 3 is firmly engaged with the housing 5 by both the fixing hole 35 and the engagement portion 31, movement of the terminal member 3 is assuredly restricted even when the lead wire 13 is pulled toward the rear end side.

Therefore, a load is less likely to act on a joint portion where the terminal member 3 and the circuit board 7 are joined to each other by means of soldering, so that a significant effect that an electrical connection between the terminal member 3 and the circuit board 7 is less likely to be broken, is achieved.

(2) In the first embodiment, the electrical connection is not an electrical connection established through contact between a male terminal and a female terminal as in the conventional art, and thus an increase in contact resistance can be inhibited. That is, loss of signal transmission between the sensor 15 and the circuit board 7 is less likely to occur, and thus there is an effect that the accuracy of measurement by the sensor 15 is high.

(3) In the first embodiment, surface treatment as in a contact portion between the male terminal and the female terminal in the conventional art can be omitted, and it is also possible to reduce the number of components.

(4) In the first embodiment, the circuit connection portion 23 is bent at the first bent portion 33 and the second bent portion 34. In addition, the width of the intermediate portion 25 of the terminal member 3 is larger than the width of the circuit connection portion 23 and larger than the width of the groove 51 of the through hole 41.

Therefore, in the case of inserting the terminal member 3 through the through hole 41 of the housing 5, the terminal member 3 can be attached to the housing 5 without taking an incorrect top-bottom orientation, by passing the bent portions of the terminal member 3 through the groove 51 of the through hole 41.

(5) In the first embodiment, since the front end side of the circuit connection portion 23 is bent in the projection direction of the engagement portion 31, the front end side of the circuit connection portion 23 can easily be connected to the circuit board 7.

(6) In the first embodiment, since the annular seal member 27 having elasticity is externally fitted on the lead wire 13, the through hole 41 can be sealed (made watertight) by press-fitting the seal member 27 into the through hole 41 (specifically, the lead wire insertion hole 42).

(7) In the first embodiment, in the housing 5, the part of the upper surface 45a of the protrusion portion 45 and the part of the lower surface 41a of the through hole 41 have the same flat surface H, and the projection portion 49 is provided on the same flat surface H of the protrusion portion 45.

Therefore, movement of the terminal member 3 inserted through the through hole 41 is restricted by the projection portion 49 outside the through hole 41. Furthermore, since the projection portion 49 is provided outside the through hole 41, the height of the projection portion 49 is not restricted by the height of the through hole 41 and can be set to an appropriate height (i.e., an appropriate height at which engagement between the fixing hole 35 and the projection portion 49 is not released).

(8) In the first embodiment, when the projection portion 49 is fitted in the fixing hole 35, movement of the intermediate portion 25 of the terminal member 3 in the thickness direction is restricted by both step portions 53a and 53b.

Thus, there is an advantage that the terminal member 3 is less likely to drop off from the housing 5.

[1-7. Correspondence of Wording]

The terminal member 3, the housing 5, the circuit board 7, the connector 11, the lead wire 13, the lead wire connection portion 21, the circuit connection portion 23, the intermediate portion 25, the seal member 27, the engagement portion 31, the fixing hole 35, the first bent portion 33, the second bent portion 34, the through hole 41, the protrusion portion 45, the front end surface 45b, the projection portion 49, the groove 51, the step portions 53a and 53b, and the third bent portion 55 in the first embodiment correspond to examples of a terminal member, a housing, a circuit board, a connector, a lead wire, a lead wire connection portion, a circuit connection portion, an intermediate portion, a seal member, an engagement portion, a fixing hole, a first bent portion, a second bent portion, a through hole, a protrusion portion, an engaged portion, a projection portion, a groove, a step portion, and a third bent portion, respectively, in the present invention.

2. Second Embodiment

Next, a second embodiment will be described. The description with the same contents as those in the first embodiment is omitted or simplified. For the same components as those in the first embodiment, the same reference numerals are used.

A connector of the second embodiment is a connector in which terminal members are fixed to a housing similarly to the first embodiment. Hereinafter, each component will be described in detail.

[2-1. Terminal Members]

First, the terminal members will be described.

Figure 14A:
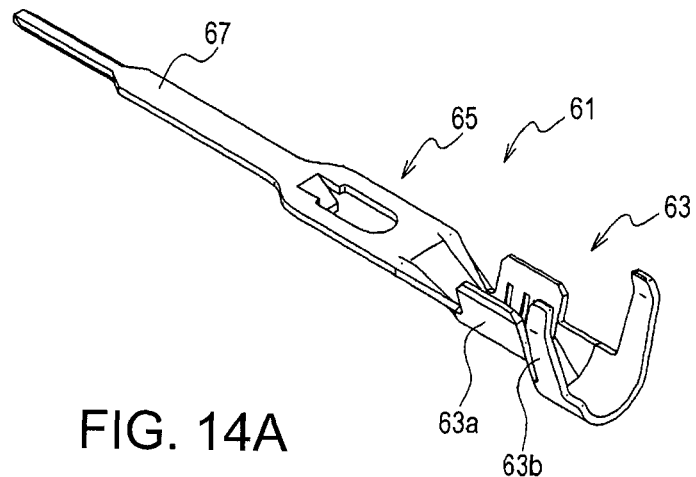
FIG. 14A is a perspective view of a terminal member of a second embodiment.
Figure 14B:
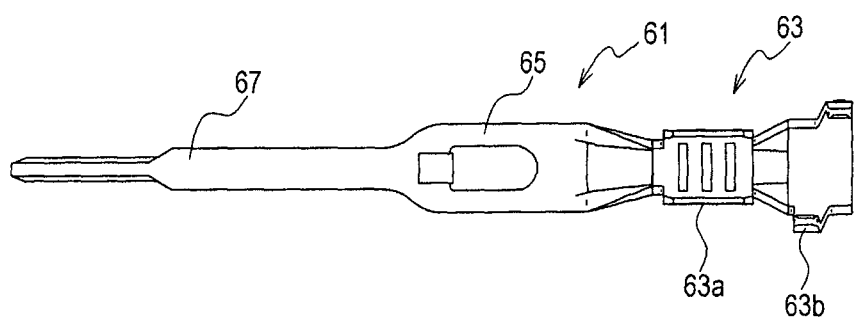
FIG. 14B is a plan view of the terminal member.
Figure 14C:
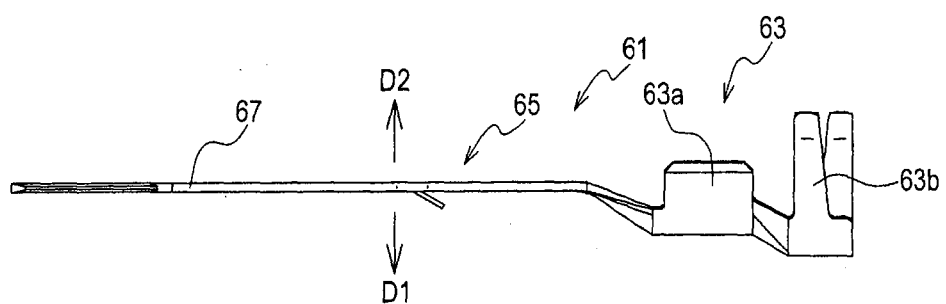
FIG. 14C is a front view of the terminal member.

As shown in FIGS. 14A-14C, similarly to the first embodiment, a terminal member 61 used in the second embodiment includes a lead wire connection portion 63 at a rear end side thereof (the right side in FIG. 14B), includes a plate-like circuit connection portion 67 at a front end side thereof (the left side in FIG. 14B), and further includes a plate-like intermediate portion 65 between the lead wire connection portion 63 and the circuit connection portion 67.

Similarly to the first embodiment, the lead wire connection portion 63 includes core wire connection portions 63a for fixing and holding a lead wire 13, and seal member holding portions 63b for holding a seal member 27.

Particularly, in the second embodiment, the front end side of the lead wire connection portion 63 extends obliquely upward (upward in FIG. 14C), and the intermediate portion 65 and the circuit connection portion 67 extend straight in the longitudinal direction of the terminal member 61 (the right-left direction in FIG. 14C) from the front end of the lead wire connection portion 63 toward the front end side.

Figure 15A:
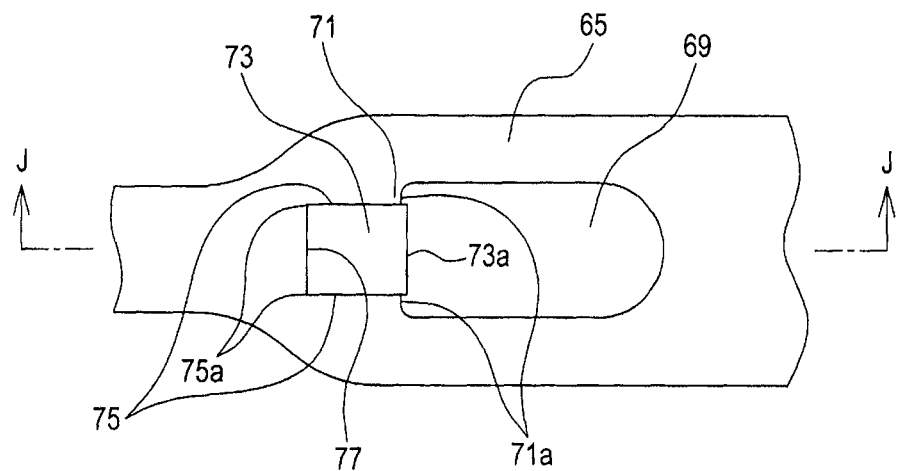
FIG. 15A is a plan view showing a part of an intermediate portion of the terminal member.
Figure 15B:
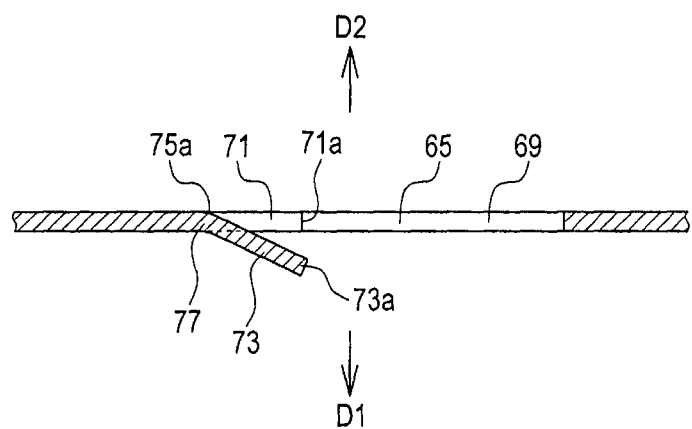
FIG. 15B is a J-J cross-sectional view of FIG. 15A.

In addition, as shown in FIGS. 15A and 15B in an enlarged manner, an engagement portion 73 projecting toward the lower side in the thickness direction of the intermediate portion 65 (the lower side in FIG. 15B) is provided at an end portion 71 at the front end side (the left side in FIG. 15) of a fixing hole 69 provided in the intermediate portion 65. Hereinafter, the lower side in FIG. 15B is referred to as first direction D1, and the side opposite thereto is referred to as second direction D2.

Specifically, as shown in FIG. 15A, a pair of parallel slits 75 are present in the end portion 71 along a longitudinal direction (the right-left direction in FIG. 15A) so as to reach the fixing hole 69. Between the slits 75, the engagement portion 73 having a width shorter than the width (the dimension in the up-down direction in FIG. 15A) of the fixing hole 69 projects obliquely downward (toward the lower side in FIG. 15B), for example, at an inclination of approximately 30 degrees relative to the intermediate portion 65 as shown in FIG. 15B.

The engagement portion 73 is a rectangular plate, and is bent at the position of start portions 75a of the slits 75 in the intermediate portion 65 and projects straight obliquely downward. The portion at which the engagement portion 73 is bent is a base portion 77 of the engagement portion 73.

Figure 16A:
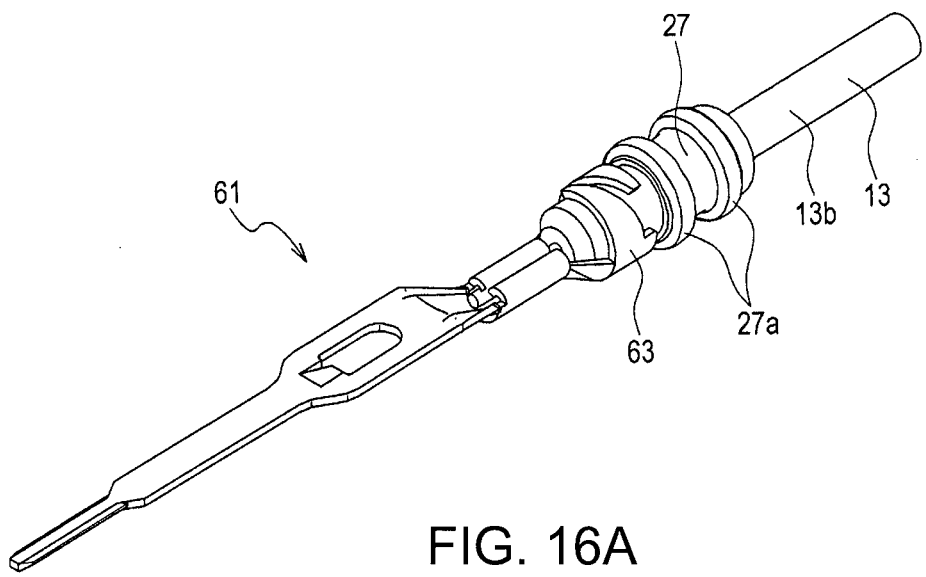
FIG. 16A is a perspective view showing an upper surface side of the terminal member to which a lead wire is connected.
Figure 16B:
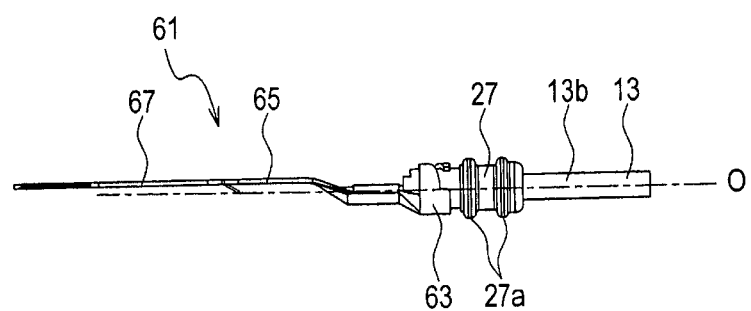
FIG. 16B is a front view of the terminal member.

In addition, as shown in FIGS. 16A and 16B, similarly to the first embodiment, the lead wire 13 is connected to the lead wire connection portion 63, and the annular seal member 27 is externally fitted on a coating portion 13b of the lead wire 13. The seal member 27 has a cylindrical shape similarly to the first embodiment, and an annular projection portion 27a is formed on the outer peripheral surface of the seal member 27, along the circumferential direction of the seal member 27, and at two locations.

In the second embodiment, the circuit connection portion 67 and the intermediate portion 65 are disposed at the upper side (the upper side in the FIG. 16B: in the second direction D2) with respect to an axial center O of the lead wire 13 and the seal member 27. In other words, the axial center O is located at the lower side in the thickness direction (in the first direction D1) with respect to the circuit connection portion 67 and the intermediate portion 65.

[2-2. Connector]

Next, the connector will be described.

Figure 17A:
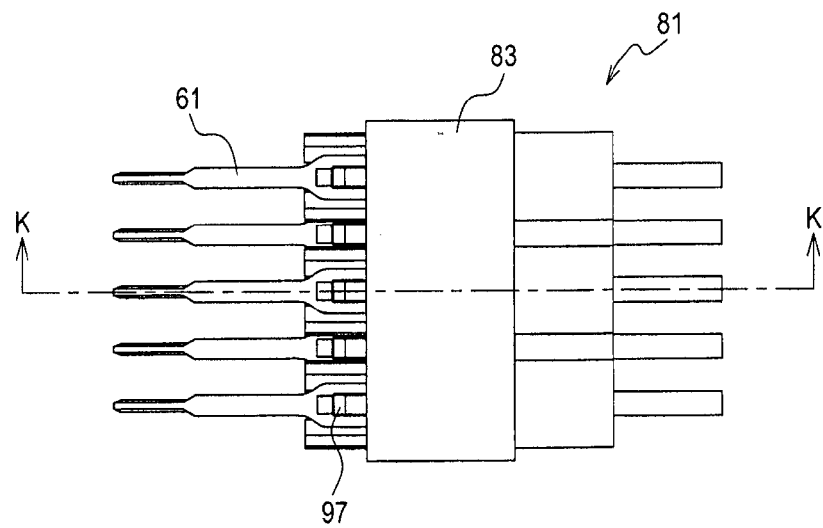
FIG. 17A is a plan view showing a connector (to which five terminal members are attached) of the second embodiment.
Figure 17B:
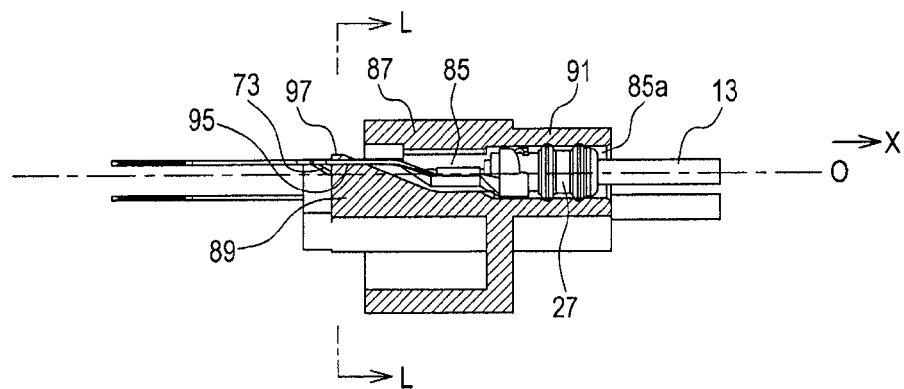
FIG. 17B is a K-K cross-sectional view of FIG. 17A.
Figure 17C:
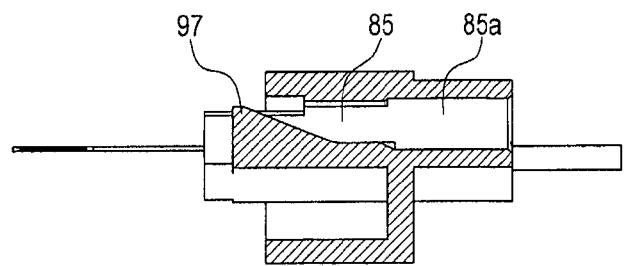
FIG. 17C is a cross-sectional view showing a state where a part of the terminal members are removed from the K-K cross-section of FIG. 10B.

As shown in FIGS. 17A-17C, a connector 81 of the second embodiment is a connector in which terminal members 61 are fixed to a housing 83 made of a resin.

Similarly to the first embodiment, a plurality of (here, five) through holes 85 through which a plurality of (here, five) terminal members 61 are inserted are formed in the housing 83 so as to penetrate the housing 83 in an axial direction (penetration direction: the right-left direction in FIG. 17).

Specifically, as shown in FIG. 17B, the housing 83 includes a tubular center portion 87, a protrusion portion 89 at a front end side (the left side in FIG. 17A) with respect to the center portion 87, and a tubular seal portion 91 at a rear end side with respect to the center portion 87. The through holes 85 are provided so as to penetrate the center portion 87 and the tubular seal portion 91.

In the tubular seal portion 91, lead wire insertion holes 85a into each of which the lead wire 13 and the seal member 27 are inserted are formed as parts of the through holes 85.

Specifically, the tubular seal portion 91 is a portion in which the seal member 27 through which the lead wire 13 is inserted is press-fitted and held in each lead wire insertion hole 85a thereof. Here, the seal member 27 has a cylindrical shape having the annular projection portions 27a on the outer peripheral surface thereof. Thus, the cross-sectional shape (a cross-section perpendicular to the axial center O) of each lead wire insertion hole 85a of the tubular seal portion 91 is also formed as a cylindrical hollow shape according to the outer periphery of the seal member 27 (specifically, the outer peripheries of the annular projection portions 27a).

In the connector 81, the axial center of each lead wire insertion hole 85a and the axial center of the lead wire 13 and the seal member 27 coincide with each other, and thus are referred to as the same axial center O below.

Figure 18A:
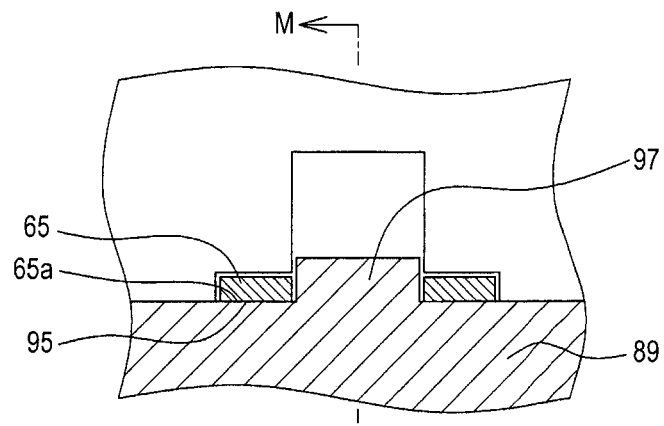
FIG. 18A is a cross-sectional view showing a part of an L-L cross-section of FIG. 17A in an enlarged manner.

As shown in FIG. 18A, an upper surface (a surface at the upper side in FIG. 18A) 95 of the protrusion portion 89 is flat such that the plate-like intermediate portion 65 of the terminal member 61 is brought into contact therewith, and a projection portion 97 projecting upward is formed on the upper surface 95. Similarly to the first embodiment, the projection portion 97 is fitted into the fixing hole 69 of the terminal member 61 in attaching the terminal member 61 to the housing 83. A lower surface 65a of the intermediate portion 65 and the upper surface 95 of the protrusion portion 89 oppose each other.

Figure 18B:
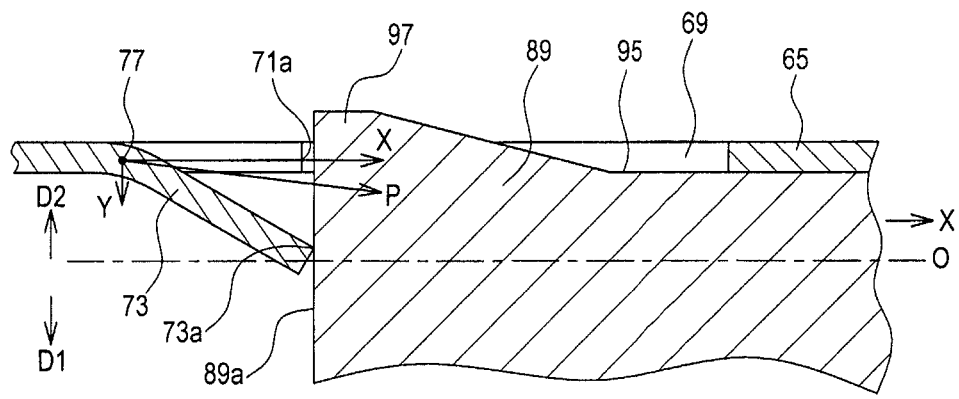
FIG. 18B is an M-M cross-sectional view of FIG. 18A.

In addition, as shown in FIG. 18B, a distal end 73a of the engagement portion 73 extending from the intermediate portion 65 is in contact and engaged with a front end surface 89a of the protrusion portion 89 in a state where the projection portion 97 of the protrusion portion 89 is fitted in the fixing hole 69 of the intermediate portion 65.

Particularly, in the second embodiment, the upper surface 95 of the protrusion portion 89 extends at the radially outer side (i.e., at the upper side in FIG. 17B and FIG. 18B: the second direction D2) with respect to the axial center O of the lead wire insertion hole 85a of the tubular seal portion 91. Furthermore, the base portion 77 of the engagement portion 73 is also displaced from the axial center O of the lead wire insertion hole 85a and disposed at the upper side (in the second direction D2) with respect to the axial center O.

In addition, the distal end 73a of the engagement portion 73 is located at the axial center O side with respect to the base portion 77, that is, at the side opposite to the side at which the upper surface 95 of the protrusion portion 89 extends (at the lower side in FIG. 18B).

When the above-described condition for arrangement of the upper surface 95 of the protrusion portion 89 and the base portion 77 of the engagement portion 73 (i.e., being located at the second direction D2 side with respect to the axial center O) is satisfied, the position of the distal end 73a of the engagement portion 73 may be displaced from the position shown in FIG. 18B.

Figure 19A:
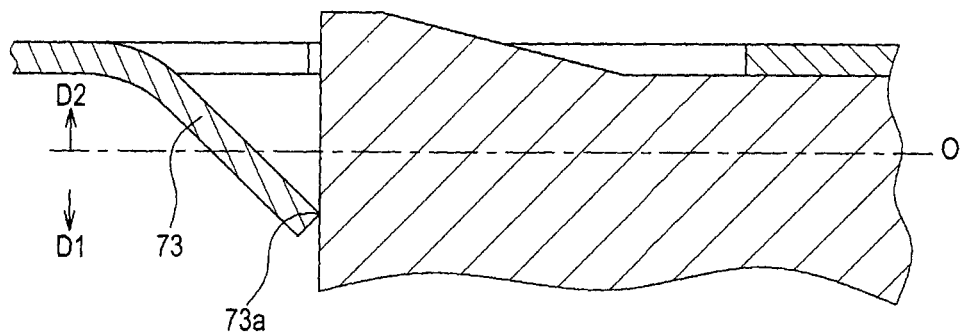
FIGS. 19A and 19B are cross-sectional views (cross-sectional views at the same position as that of the M-M cross-section) showing a modification of an engagement portion of the terminal member of the second embodiment.
Figure 19B:
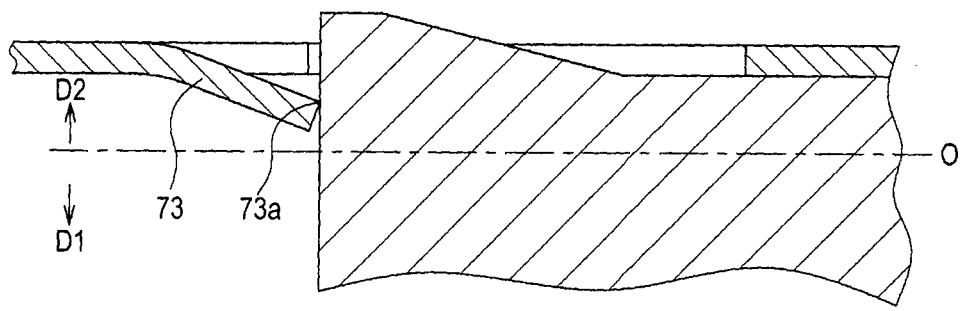

The distal end 73a of the engagement portion 73 may be located at the lower side (in the first direction D1) with respect to the axial center O, for example, as shown in FIG. 19A, or may be located at the upper side (in the second direction D2) with respect to the axial center O, for example, as shown in FIG. 19B.

[2-3. Advantageous Effects]

In the second embodiment, the same advantageous effects as those in the first embodiment are achieved.

Particularly, in the second embodiment, the upper surface 95 of the protrusion portion 89 extends at the upper side (in the second direction D2) with respect to the axial center O of the lead wire insertion hole 85a of the tubular seal portion 91, and the base portion 77 of the engagement portion 73 is also displaced from the axial center O of the lead wire insertion hole 85a and disposed at the upper side (in the second direction D2) with respect to the axial center O.

Therefore, even when the lead wire 13 attached to the housing 83 is pulled with great force in an arrow X direction (see FIG. 18C), the engagement portion 73 of the terminal member 61 is less likely to be disengaged from the front end surface 89a of the protrusion portion 89. That is, there is an advantageous effect that the terminal member 61 is less likely to drop off from the housing 83.

That is, since the lead wire 13 is disposed along the axial center O, when the lead wire 13 is pulled with great force in the arrow X direction, the lead wire connection portion 63 of the terminal member 61 connected to the lead wire 13, etc. are also pulled along the axial center O.

Figure 18C:
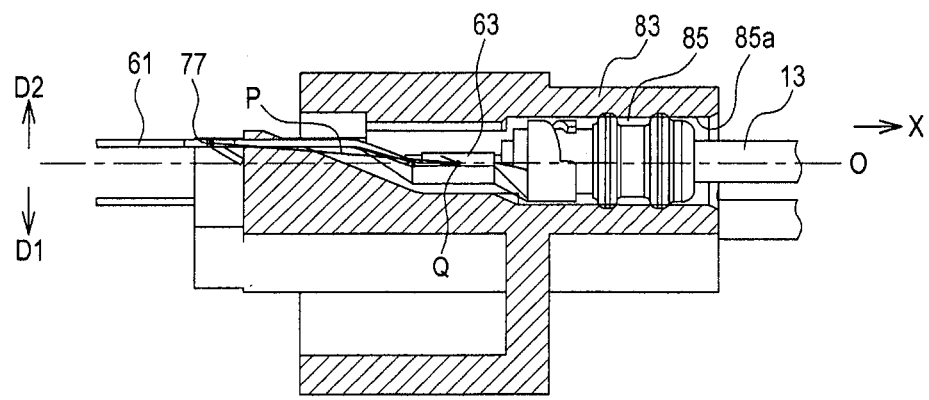
FIG. 18C is a cross-sectional view showing a part of FIG. 17B in an enlarged manner.

However, in the second embodiment, since the base portion 77 of the engagement portion 73 is disposed at the upper side (in the second direction D2) with respect to the axial center O as shown in FIGS. 18B and 18C, when the lead wire connection portion 63 is pulled in the arrow X direction along the axial center O, the pulling force acts in an arrow P direction (i.e., a direction of a portion Q at which the lead wire 13 is connected) in the base portion 77. Therefore, in the base portion 77, components of the force applied in the arrow P direction are applied not only in the arrow X direction but also in an arrow Y direction perpendicular to the arrow X direction.

The portion Q at which the lead wire 13 is connected to the terminal member 61 is actually a surface mainly in contact at the core wire connection portions 63a, but is simply shown as one point in FIG. 18C.

The Y direction is the downward direction in FIG. 18B, and is the direction opposite to the upward direction in which the engagement portion 73 is disengaged from the front end surface 89a. Thus, the engagement portion 73 receives force toward the axial center O and becomes less likely to be disengaged from the front end surface 89a.

As described above, in the second embodiment, a significant effect is achieved that, when the lead wire 13 is pulled in the arrow X direction, the terminal member 61 becomes less likely to drop off from the housing 83 due to a component of the force.

3. Other Embodiments

The present invention is not limited to the above embodiments in any way, and it is needless to say that the present invention can be carried out in various modes without departing from the scope of the present invention.

(1) For example, the shapes of the terminal member and the housing or the shapes of the projection portion and the engagement portion are not limited to the shapes in the above embodiments. The engagement portion provided to the terminal member is not limited to the flaky engagement portion as in the first and second embodiments. An engagement portion projecting in the thickness direction may be provided, for example, by pressing and plastically deforming a part of the intermediate portion along the front outer edge of the fixing hole in the thickness direction of the intermediate portion.

(2) For example, the numbers of the terminal members and the through holes are not limited to the numbers in the above embodiments.

(3) Furthermore, for example, the arrangement of the plurality of through holes is not limited to the two-row arrangement in the above embodiments. For example, all the through holes may be arranged in one row (e.g., in one row in the right-left direction in FIG. 8A). Alternatively, the through holes may be arranged in three or more rows.

(4) The function of one component in each of the above embodiments may be shared by a plurality of components, or the functions of a plurality of components may be performed by one component. In addition, a part of the configuration in each of the above embodiments may be omitted. Moreover, for example, at least a part of the configuration in each of the above embodiments may be added to or may replace a configuration in another embodiment. It is noted that all aspects included in the technical idea specified by the wording of the claims are embodiments of the present invention.

DESCRIPTION OF REFERENCE NUMERALS 3, 61: terminal member
5, 83: housing
7: circuit board
11, 81: connector
13: lead wire
21, 83: lead wire connection portion
23, 67: circuit connection portion
25, 65: intermediate portion
27: seal member
31, 73: engagement portion
33: first bent portion
34: second bent portion
35, 69: fixing hole
35a, 71: end portion
41, 85: through hole
42, 85a: lead wire insertion hole
45, 89: protrusion portion
45a, 95: upper surface
45b, 89a: front end surface
49, 97: projection portion
51: groove
53a, 53b: step portion
55: third bent portion
77: base portion

The invention claimed is:

1. A long terminal member formed from a metal plate, the terminal member comprising:
a lead wire connection portion provided at a rear end side;
a circuit connection portion provided at a front end side for electrical connection to a circuit board; and
an intermediate portion located between the lead wire connection portion and the circuit connection portion, wherein
the intermediate portion has a fixing hole penetrating the intermediate portion in a thickness direction and containing an end portion at the front end side of the fixing hole,
an engagement portion projecting in the thickness direction is provided at the end portion of the fixing hole, and
the circuit connection portion has a first bent portion that is bent to a side opposite to a projection direction of the engagement portion, and a second bent portion that is bent to the front end side in a longitudinal direction of the terminal member at the front end side with respect to the first bent portion.

2. The terminal member according to claim 1, wherein the circuit connection portion has a third bent portion that is bent in the projection direction of the engagement portion at the front end side with respect to the second bent portion of the circuit connection portion.

3. The terminal member according to claim 1, further comprising a lead wire, wherein the lead wire is connected to the lead wire connection portion.

4. The terminal member according to claim 3, wherein an annular seal member is externally fitted on the lead wire.

5. A connector in which the terminal member according to claim 1 is attached to a housing having an electrical insulation property, wherein
the housing has a through hole penetrating from the lead wire side to the circuit board side, and the terminal member is inserted in the through hole,
the housing has a surface provided along the intermediate portion of the terminal member inserted in the through hole, the surface opposing the intermediate portion,
a front end side of the terminal member projects from an opening at the circuit board side of the through hole, and the engagement portion of the terminal member is engaged with the housing, and the surface is provided so as to extend at a radially outer side with respect to an axial center of a lead wire insertion hole at a side at which the lead wire is inserted, of the through hole, and at least a base portion projecting from the intermediate portion, of the engagement portion, is disposed at a side at which the surface extends, with respect to the axial center of the lead wire insertion hole.

6. The connector according to claim 5, wherein the housing includes a projection portion that is fitted in the fixing hole of the terminal member, and an engaged portion with which the engagement portion of the terminal member is engaged.

7. The connector according to claim 1, wherein the intermediate portion has a plate form.

8. A connector in which the terminal member according to claim 1 is attached to a housing having an electrical insulation property, wherein
the housing has a through hole penetrating from the lead wire side to the circuit board side, and the terminal member is inserted in the through hole, and
a front end side of the terminal member projects from an opening at the circuit board side of the through hole, and the engagement portion of the terminal member is engaged with the housing.

9. The connector according to claim 8, wherein the housing includes a projection portion that is fitted in the fixing hole of the terminal member, and an engaged portion with which the engagement portion of the terminal member is engaged.

10. The connector according to claim 9, wherein movement of the terminal member toward the rear end side is restricted by the projection portion being engaged with the end portion at the front end side of the fixing hole of the terminal member.

11. The connector according to claim 9, wherein movement of the terminal member toward the rear end side is restricted by the engagement portion being engaged with the engaged portion of the housing.

12. The connector according to claim 8, wherein
the through hole of the housing includes a groove that allows a portion of the terminal member between the first bent portion and the second bent portion to pass therethrough and is provided along a penetration direction of the through hole and at a position opposite to a position at which the projection portion is disposed.

13. The connector according to claim 12, wherein a width of the intermediate portion in the terminal member is larger than a width of the circuit connection portion and a width of the groove of the through hole, and the width of the circuit connection portion is smaller than the width of the groove of the through hole.

14. The connector according to claim 8, wherein the housing has a protrusion portion projecting toward the circuit board side, and a part of a surface of the protrusion portion and a part of an inner peripheral surface of the through hole have the same flat surface.

15. The connector according to claim 14, wherein the projection portion is provided on the part of the surface of the protrusion portion that is the same flat surface.

16. The connector according to claim 15, wherein a distance from the same flat surface to a pair of step portions forming both sides in a width direction of the groove of the through hole of the housing is equal to or less than a distance from the same flat surface to the projection portion.

17. The connector according to claim 8, wherein the through hole of the housing is sealed by a seal member externally fitted on the lead wire.

* * * * *